US012758539B2

(12) United States Patent
Chawla et al.

(10) Patent No.: US 12,758,539 B2
(45) Date of Patent: Oct. 13, 2026

(54) METHOD OF TREATING AN AUTOIMMUNE HEMATOLOGICAL DISORDER

(71) Applicant: Novartis AG, Basel (CH)

(72) Inventors: Raghav Chawla, Bottmingen (CH); Thomas Holbro, Basel (CH); Guido Junge, Basel (CH); Anna Svenja Schubart Wellensiek, Allschwil (CH)

(73) Assignee: NOVARTIS AG, Basel (CH)

( * ) Notice: Subject to any disclaimer, the term of this patent is extended or adjusted under 35 U.S.C. 154(b) by 350 days.

(21) Appl. No.: 18/569,432

(22) PCT Filed: Jun. 17, 2022

(86) PCT No.: PCT/IB2022/055639
§ 371 (c)(1),
(2) Date: Dec. 12, 2023

(87) PCT Pub. No.: WO2022/264101
PCT Pub. Date: Dec. 22, 2022

(65) Prior Publication Data

US 2024/0277689 A1 Aug. 22, 2024

Related U.S. Application Data

(60) Provisional application No. 63/212,465, filed on Jun. 18, 2021.

(51) Int. Cl.
*A61K 31/454* (2006.01)

(52) U.S. Cl.
CPC .................................. *A61K 31/454* (2013.01)

(58) Field of Classification Search
CPC . A61K 31/454; A61P 7/00; A61P 7/06; A61P 37/02
USPC .......................................................... 514/323
See application file for complete search history.

(56) References Cited

U.S. PATENT DOCUMENTS

| | | | |
|---|---|---|---|
| 5,312,925 | A | 5/1994 | Allen et al. |
| 2016/0152605 | A1 | 6/2016 | Adams et al. |

FOREIGN PATENT DOCUMENTS

| | | | |
|---|---|---|---|
| CN | 117210426 | A | 12/2023 |
| EP | 4194451 | A1 | 6/2023 |
| EP | 4389742 | A1 | 6/2024 |
| WO | 2011109526 | A1 | 9/2011 |
| WO | 2011153221 | A1 | 12/2011 |
| WO | 2015009616 | A1 | 1/2015 |
| WO | 2015168635 | A2 | 11/2015 |
| WO | 2017109208 | A1 | 6/2017 |
| WO | 2019043609 | A1 | 3/2019 |
| WO | 2019227102 | A1 | 11/2019 |
| WO | 2021234544 | A1 | 11/2021 |

OTHER PUBLICATIONS

Wikipedia , List of autoimmune diseases, Jan. 9, 2019, p. 1-20 (Year: 2019).*

(Continued)

*Primary Examiner* — Taylor V Oh
(74) *Attorney, Agent, or Firm* — Adil R. Zhugralin

(57) ABSTRACT

Described herein are methods of treating an autoimmune benign hematological disorder (e.g., ITP, CAD, wAIHA, and TTP) with the Factor B inhibitor LNP023 (iptacopan) or a pharmaceutically acceptable salt thereof, e.g. iptacopan hydrochloride.

22 Claims, 8 Drawing Sheets

(56) References Cited

OTHER PUBLICATIONS

Kishida, Simultaneous control of particle size and shape in crystallisation of ecabet sodium hydrate, and mechanism of same, Osaka City University, A-3783, 1-17, 2019.

Organic Compound Crystal Production Handbook—Principles and Know-how, 57-79, Jul. 25, 2008.

Berentsen et al, Novel insights into the treatment of complement-mediated hemolytic anemias, www.ncbi.nlm.nih.gov, Sep. 9, 2019, 1-20, 10.

Jang et al, 63rd ASH annual meeting abstracts poster abstracts 508.bone marrow failure 12-month analysis of a phase 2 study of iptacopan (LNP023) monotherapy for paroxysmal nocturnal hemoglobinuria, blood, Nov. 5, 2021, 2173-2175, 138.

Jang et al, Iptacopan monotherapy in patients with paroxysmal nocturnal jemoglobinuria: a 2-cohort open-label proof-of-concept study, Blood Advances, Nov. 12, 2021_, 4450-4460, 6.

Risitano et al, Addition of iptacopan, an oral factor B inhibitor, to eculizumab in patients with paroxysmal nocturnal haemogliobinuria and active haemolysis: an open-label, single-arm, phase 2, proof-of-concept trial, The Lancet Haematology, Mar. 22, 2021, e-344-e354, 8.

Schubart, et al., Small-molecule factor B inhibitor for the treatment of complement-mediated diseases, PNAS, Apr. 16, 2019, 7926-7931, 116(16).

Mainolfi, et al., Discovery of 4-((2S,4S)-4-Ethoxy-1-((5-methoxy-7-methyl-1H-indol-4-yl)methyl)piperidin-2-yl) benzoic Acid (LNP023), a Factor B Inhibitor Specifically Designed To Be Applicable to Treating a Diverse Array of Complement Mediated Diseases, Journal of Medicinal Chemistry, 63, 5697-5722, 2020.

Webb, et al., LNP023: A novel oral complement alternative pathway factor B inhibitor for the treatment of glomerular disease, Nephrology Dialysis Transplantation, MO042, 142, 2020.

Voytsekhovsky, et al., Thrombocytopenia, Amur Medical Journal, 2, 7-25, 2017.

Clinical Trial NCT05268289, Feb. 24, 2022, available at https://www.clinicaltrials.gov/study/NCT05268289.

Mohite, et al., BF3Et2O and trifluoroacetic acid/triethyl amine-mediated synthesis of functionalized piperidines, Tetrahedron Letters, 53, 30-35, 2012.

Risitano, et al., Therapeutic complement inhibition in complement-mediated hemolytic anemias: Past, present and future, Seminars in Immunology, 28, 223-240, Jun. 23, 2016.

Fakhouri, et al., Terminal Complement Inhibitor Eculizumab in Adult Patients With Atypical Hemolytic Uremic Syndrome: A Single-Arm, Open-Label Trial, American Journal of Kidney Diseases, 68(1), 84-93, 2016.

Zhang, et al., Atypical Hemolytic Uremic Syndrome: A Brief Review, Hematology Reports, 9, 7053, 2017.

Roth, et al., Red cells and erythropoiesis, excluding iron, Blood, 2024, 144, 2457-2458.

Science Daily, Abatacept found ineffective in treatment of non-life threatening lupus, trial results show, Sep. 28, 2010, retrieved from www.sciencedaily.com/releases/2010/09/100928111246.htm.

Ispasanie, et al., Alternative Complement Pathway Inhibition Does Not Abrogate Meningococcal Killing by Serum of Vaccinated Individuals, Sec. Microbial Immunology, 12(Article 747594), 11 pages, Oct. 8, 2021.

* cited by examiner

FIG. 2

| Period | Screening | | Treatment | | | | | | | | | | Follow-up/Washout | | | | |
|---|---|---|---|---|---|---|---|---|---|---|---|---|---|---|---|---|---|
| Visit Name | Screening | Baseline | Treatment | | | | | | | | | EOT | FU | | | EOS Part A/Day 1 Part B | Post Study Safety Contact |
| Visit Numbers[1] | 1 | 20 | 100 | 110[2] | 120 | | 130[2] | 140 | 150[2] | 160[2] | 170[2] | 180 | 190[2] | 200 | 210[2,3] | 1999[4] | |
| Days | -35 to -4 | -7 to -2 | 1 | 8 | 15 | | 22 | 29 | 43 | 57 | 71 | 85 | 92 | 99 | 106 | 113 | 115 |
| Months | -2 to -1 | -1 | 1 | 1 | 1 | | 1 | 1 | 2 | 2 | 3 | 3 | 4 | 4 | 4 | 4 | 4 |
| Weeks | -5 to -1 | -1 | 0 | 1 | 2 | | 3 | 4 | 6 | 8 | 10 | 12 | 13 | 14 | 15 | 16 | 16 |
| Time (post-dose) | - | - | - | - | 0h | 2h | - | - | - | 0h | - | - | - | - | - | - | - |
| Informed consent | X | | | | | | | | | | | | | | | | |
| Genetic consent | X | | | | | | | | | | | | | | | | |
| Inclusion / Exclusion criteria | X | X | | | | | | | | | | | | | | | |
| Medical history/current medical conditions | X | | | | | | | | | | | | | | | | |
| Prior medications | X | | | | | | | | | | | | | | | | |
| Vaccination | X | | | | | | | | | | | | | | | | |
| Demography | X | | | | | | | | | | | | | | | | |
| Hepatitis and HIV Screen | S | | | | | | | | | | | | | | | | |
| Body Height | X | | | | | | | | | | | | | | | | |
| Body Weight | X | | X | | X | | | X | | X | | X | | | | X | |
| Physical Examination | S | | S | | | | | S | | | | S | | | | S | |
| Body Temperature | X | X | X | X | X | | X | X | X | X | X | X | X | X | | X | |

FIG. 2 continuation

| Period | Screening | | Treatment | | | | | | | | | | | Follow-up/Washout | | | | |
|---|---|---|---|---|---|---|---|---|---|---|---|---|---|---|---|---|---|
| Visit Name | Screening | Baseline | Treatment | | | | | | | | | EOT | FU | | | EOS Part A/Day 1 Part B | Post Study Safety Contact |
| Visit Numbers[1] | 1 | 20 | 100 | 110[2] | 120 | | 130[2] | 140 | 150[2] | 160[2] | 170[2] | 180 | 190[2] | 200 | 210[2,3] | 1999[4] | |
| Days | -35 to -4 | -7 to -2 | 1 | 8 | 15 | | 22 | 29 | 43 | 57 | 71 | 85 | 92 | 99 | 106 | 113 | 115 |
| Months | -2 to -1 | -1 | 1 | 1 | 1 | | 1 | 1 | 2 | 2 | 3 | 3 | 4 | 4 | 4 | 4 | 4 |
| Weeks | -5 to -1 | -1 | 0 | 1 | 2 | | 3 | 4 | 6 | 8 | 10 | 12 | 13 | 14 | 15 | 16 | 16 |
| Time (post-dose) | - | - | - | - | 0h | 2h | - | - | - | 0h | - | - | - | - | - | - | - |
| Blood Pressure | X | | X | | X | X | | X | | | | X | | | | X | |
| Pulse rate | X | | X | | X | X | | X | | | | X | | | | X | |
| Electrocardiogram (ECG) | X | | X | | X | X | | | | | | X | | | | X | |
| Pregnancy and assessments of fertility | S | S | | | | | | S | | S | | S | | | | S | |
| Hematology | X | X | X | X | X | | X | X | X | X | X | X | X | X | X | X | |
| Clinical Chemistry | X | | | | X | | | X | | | | X | | | | X | |
| Coagulation Panel | X | | | | X | | | X | | | | X | | | | X | |
| Urinalysis | X | | | | X | | | X | | | | X | | | | X | |
| Reproductive and thyroid hormones | X | | | | X | | | X | | | | X | | | | X | |
| Exploratory Serum Complement markers (C3, C4, Wieslab) | | X | | | X | | | | | X | | X | | | | | |

FIG. 2 continuation

| Period | Screening | | Treatment | | | | | | | | | | Follow-up/Washout | | | | |
|---|---|---|---|---|---|---|---|---|---|---|---|---|---|---|---|---|---|
| Visit Name | Screening | Baseline | Treatment | | | | | | | | | EOT | FU | | | EOS Part A/Day 1 Part B | Post Study Safety Contact |
| Visit Numbers[1] | 1 | 20 | 100 | 110[2] | 120 | | 130[2] | 140 | 150[2] | 160[2] | 170[2] | 180 | 190[2] | 200 | 210[2,3] | 1999[4] | |
| Days | -35 to -4 | -7 to -2 | 1 | 8 | 15 | | 22 | 29 | 43 | 57 | 71 | 85 | 92 | 99 | 106 | 113 | 115 |
| Months | -2 to -1 | -1 | 1 | 1 | 1 | | 1 | 1 | 2 | 2 | 3 | 3 | 4 | 4 | 4 | 4 | 4 |
| Weeks | -5 to -1 | -1 | 0 | 1 | 2 | | 3 | 4 | 6 | 8 | 10 | 12 | 13 | 14 | 15 | 16 | 16 |
| Time (post-dose) | - | - | - | - | 0h | 2h | - | - | - | 0h | - | - | - | - | - | - | - |
| Exploratory Plasma Complement markers (Factor Bb, others) | | X | | | X | | | | | X | | X | | | | | |
| PK blood collection | See table below | | | | | | | | | | | | | | | | |
| Exploratory DNA Sampling (optional) | | | X | | | | | | | | | | | | | | |
| FACIT-Fatigue | | X | | | | | | X | | X | | X | | | | | |
| Patient diary | | | X | | | | | | | | | | | | | | |
| Study drug administration | | | Daily b.i.d. | | | | | | | | | | | | | | |
| Concomitant medications | As required | | | | | | | | | | | | | | | | |
| Adverse events/SAEs | As required | | | | | | | | | | | | | | | | |

FIG. 2 continuation

| Period | Screening | | Treatment | | | | | | | | | | Follow-up/Washout | | | | |
|---|---|---|---|---|---|---|---|---|---|---|---|---|---|---|---|---|---|
| Visit Name | Screening | Baseline | Treatment | | | | | | | | | EOT | FU | | | EOS Part A/Day 1 Part B | Post Study Safety Contact |
| Visit Numbers[1] | 1 | 20 | 100 | 110[2] | 120 | | 130[2] | 140 | 150[2] | 160[2] | 170[2] | 180 | 190[2] | 200 | 210[2,3] | 1999[4] | |
| Days | -35 to -4 | -7 to -2 | 1 | 8 | 15 | | 22 | 29 | 43 | 57 | 71 | 85 | 92 | 99 | 106 | 113 | 115 |
| Months | -2 to -1 | -1 | 1 | 1 | 1 | | 1 | 1 | 2 | 2 | 3 | 3 | 4 | 4 | 4 | 4 | 4 |
| Weeks | -5 to -1 | -1 | 0 | 1 | 2 | | 3 | 4 | 6 | 8 | 10 | 12 | 13 | 14 | 15 | 16 | 16 |
| Time (post-dose) | - | - | - | - | 0h | 2h | - | - | - | 0h | - | - | - | - | - | - | - |
| Study completion information | | | | | | | | | | | | | | | | X | |
| Safety Follow up Call | | | | | | | | | | | | | | | | | X |
| Cohort 1 specific assessments | Cohort 1 specific assessments | | | | | | | | | | | | | | | | |
| sC5b-9 for stratification | X | X | | | | | | | | | | | | | | | |
| ITP-PAQ | | X | | | | | | X | | X | | X | | | | | |
| WHO bleeding score | | X | | | | | | X | | X | | X | | | | | |
| Exploratory anti-platelet antibodies | | X | | | | | | X | | | | X | | | | | |
| Immature platelet fraction[5] | | X | | | | | | X | | | | X | | | | | |
| Cohort 2 specific assessments | Cohort 2 specific assessments | | | | | | | | | | | | | | | | |

FIG. 2 continuation

| Period | Screening | | Treatment | | | | | | | | | | Follow-up/Washout | | | | |
|---|---|---|---|---|---|---|---|---|---|---|---|---|---|---|---|---|---|
| Visit Name | Screening | Baseline | Treatment | | | | | | | | | EOT | FU | | | EOS Part A/Day 1 Part B | Post Study Safety Contact |
| Visit Numbers[1] | 1 | 20 | 100 | 110[2] | 120 | | 130[2] | 140 | 150[2] | 160[2] | 170[2] | 180 | 190[2] | 200 | 210[2,3] | 1999[4] | |
| Days | -35 to -4 | -7 to -2 | 1 | 8 | 15 | | 22 | 29 | 43 | 57 | 71 | 85 | 92 | 99 | 106 | 113 | 115 |
| Months | -2 to -1 | -1 | 1 | 1 | 1 | | 1 | 1 | 2 | 2 | 3 | 3 | 4 | 4 | 4 | 4 | 4 |
| Weeks | -5 to -1 | -1 | 0 | 1 | 2 | | 3 | 4 | 6 | 8 | 10 | 12 | 13 | 14 | 15 | 16 | 16 |
| Time (post-dose) | - | - | - | - | 0h | 2h | - | - | - | 0h | - | - | - | - | - | - | - |
| Direct antiglobulin test | X | | | | | | | X | | | | X | | | | | |
| Cold agglutinin titer, cold agglutinin thermal amplitude | X | | | | | | | X | | | | X | | | | | |

[X] Assessment to be recorded in the clinical database or received electronically from a vendor

[S] Assessment to be recorded in the source documentation only

[1] Visit structure given for internal programming purpose only

[2] Visit may be performed at a remote location as allowed by local laws and regulations.

[3] Visit only applicable to treatment responders. Responders reaching a critical cut-off level during washout (as defined in Section 3.1 in the cohort specific details) will have the opportunity to skip remaining follow-up visits and move to EOS Part A/Day 1 Part B visit before completion of the 4 weeks of wash-out.

[4] The Day 1 Part B visit is on the same day as EOS for Part A. Assessments listed in the Part A assessment schedule are applicable to all participants. Assessments listed in Part B assessment schedule are in addition and only applicable to responders continuing into Part B.

[5] Measured at local labs (if available)

FIG. 3

| Period | Visit Name | Visit Numbers | Days | Months | Weeks | Time (post-dose) | PK blood collection |
|---|---|---|---|---|---|---|---|
| **Screening** | Screening | 1 | -35 to -4 | -2 to -1 | -5 to -1 | - | |
| | Baseline | 20 | -7 to -2 | -1 | -1 | - | |
| **Treatment** | Treatment | 100 | 1 | 1 | 0 | - | |
| | | 110[1] | 8 | 1 | 1 | - | |
| | | 120 | 15 | 1 | 2 | 0h | X[2] |
| | | | | | | 0.5h | X |
| | | | | | | 1h | X |
| | | | | | | 2h | X |
| | | | | | | 4h | X |
| | | | | | | 6h | X |
| | | 130[1] | 22 | 1 | 3 | - | |
| | | 140 | 29 | 1 | 4 | - | X[2] |
| | | 150[1] | 43 | 2 | 6 | - | |
| | | 160[1] | 57 | 2 | 8 | 0h | X[2] |
| | | | | | | 0.5h | X |
| | | | | | | 1h | X |
| | | | | | | 2h | X |
| | | | | | | 4h | X |
| | | | | | | 6h | X |
| | | 170[1] | 71 | 3 | 10 | - | |
| | EOT | 180 | 85 | 3 | 12 | - | |
| **Follow-up/Washout** | FU | 190[1] | 92 | 4 | 13 | - | |
| | | 200 | 99 | 4 | 14 | - | |

FIG. 3 continuation

| Period | Visit Name | Visit Numbers | Days | Months | Weeks | Time (post-dose) | PK blood collection |
|---|---|---|---|---|---|---|---|
| | | 210[1,3] | 106 | 4 | 15 | - | |
| | EOS Part A/Day 1 Part B | 1999[4] | 113 | 4 | 16 | - | |
| | Post Study Safety Contact | | 115 | 4 | 16 | - | |

[X] Assessment to be recorded in the clinical database or received electronically from a vendor

[1] Visit may be performed at a remote location as allowed by local laws and regulations.

[2] Directly before dosing

[3] Visit only applicable to treatment responders. Responders reaching a critical cut-off level during washout (as defined in Section 3.1 in the cohort specific details) will have the opportunity to skip remaining follow-up visits and move to EOS Part A/Day 1 Part B visit before completion of the 4 weeks of wash-out.

[4] The Day 1 Part B visit is on the same day as EOS for Part A. Assessments listed in the Part A assessment schedule are applicable to all participants. Assessments listed in Part B assessment schedule are in addition and only applicable to responders continuing into Part B.

METHOD OF TREATING AN AUTOIMMUNE HEMATOLOGICAL DISORDER

FIELD

Described herein are methods of treating autoimmune benign hematological disorders, and in particular, immune thrombocytopenia (ITP), cold agglutinin disease (CAD), warm autoimmune hemolytic anemia (wAIHA), and thrombic thrombocytopenic purpura (TTP), with the Factor B inhibitor LNP023 (iptacopan) or a pharmaceutically acceptable salt thereof, e.g. iptacopan hydrochloride.

BACKGROUND

Autoimmune benign hematological disorders describe a number of indications which are collectively characterized by the immune targeting and ultimate destruction of the blood cells in a subject. For example, primary immune thrombocytopenia (ITP) is an autoimmune, mostly IgG-mediated thrombocytopenia, which typically presents with signs of acute bleeding in the absence of a specific underlying cause. Though considered a rare disease, it has an estimated prevalence in the United States of 86,000 and it is the most common autoimmune hematological disorder.

Standard of care for newly diagnosed primary ITP includes administration of corticosteroids, intravenous immunoglobulins (IVIG), or anti-Rho(D) immunoglobulin. However, most adults receiving these treatments will eventually relapse and require further therapy, with subsequent treatment options including thrombopoietin receptor agonists (TPO-RA), including eltrombopag, avatrombopag and romiplostim, as well as rituximab, fostamatinib, and splenectomy. Despite these options, there continues to be an unmet medical need, namely for therapies inducing durable remissions in relapsed/refractory patients and for targeted therapies with predictive biomarkers.

Another exemplary autoimmune benign hematological disorder is primary cold agglutinin disease (CAD), which is an autoimmune hemolytic anemia often triggered by cold temperatures or viral infections. Although the term “primary” implies the absence of a specific underlying cause, recent evidence suggests that the majority of patients actually have a low-grade lymphoproliferative disorder (Berentsen S et al (2019) *J Blood Med* p. 93-103). Primary CAD is a rare disease with an estimated prevalence in the United States of 5,000, and usually manifests acutely with signs and symptoms of hemolytic anemia. Primary CAD almost exclusively affects adults, with a median age of 67 years at presentation.

Standard of care for acute primary CAD includes plasmapheresis, intravenous immunoglobulins (IVIG), and/or red blood cell transfusions. The main treatment option for refractory cases consists of rituximab, with or without bendamustine. Despite these options, there continues to be an unmet medical need, namely for therapies inducing durable remissions in relapsed/refractory patients and for targeted therapies with predictive biomarkers.

Iptacopan (LNP023) is an orally administered, small molecular weight, first-in-class, selective protease inhibitor that binds to complement Factor B (FB) and inhibits C3- (i.e., C3bBb) and C5 (C3bBbC3b) convertases, thereby blocking the formation of the membrane attack complex (MAC). In addition, iptacopan blocks the cellular amplification phase and halts the complement activation process. In multiple in vitro and in vivo non-clinical mechanistic studies, iptacopan has demonstrated inhibition of the complement alternative pathway (Schubart A, et al. (2019) *Proc Natl Acad Sci USA;* 116(16):7926-31). As such, iptacopan is likely to provide therapeutic benefit for treatment of autoimmune benign hematological disorders in a subject, particularly for ITP and CAD patients.

SUMMARY

Described herein are methods of treating an autoimmune benign hematological disorder, and in particular, immune thrombocytopenia (ITP), cold agglutinin disease (CAD), warm autoimmune hemolytic anemia (wAIHA), and thrombic thrombocytopenic purpura (TTP), with LNP023 (iptacopan) or a pharmaceutically acceptable salt thereof, e.g. iptacopan hydrochloride. Further, the disclosure relates to a proof of concept, adaptive basket Phase 2 study to determine safety and efficacy of iptacopan or a pharmaceutically acceptable salt thereof, e.g., iptacopan hydrochloride, in a subject with ITP or CAD. In an embodiment, the subject has or is diagnosed with high complement activation or low complement activation. In an embodiment, the subject has or is diagnosed with thrombocytopenia, anemia, or hemolysis. In an embodiment, the patients are treatment naive to complement inhibitor therapy, including anti-C5 antibody therapy. In an embodiment, the patients have been previously treated, or are currently being treated, with complement inhibitor therapy, immunosuppressive therapy, or other therapy prescribed for the treatment of ITP or CAD.

The disclosure also relates to pharmaceutical compositions, uses, kits, etc. related to iptacopan or a pharmaceutically acceptable salt thereof, e.g., iptacopan hydrochloride.

Iptacopan belongs to the class of Factor B inhibitors of the complement pathway and acts by inhibiting or suppressing the amplification of the complement system caused by C3 activation irrespective of the initial mechanism of activation.

Iptacopan is chemically designated as 4-((2S,4S)-(4-ethoxy-1-((5-methoxy-7-methyl-1H-indol-4-yl)methyl)piperidin-2-yl))benzoic acid and can be represented by the following chemical structure:

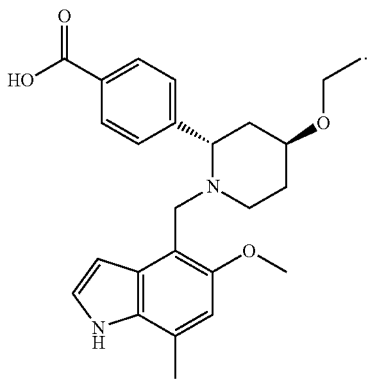 [SMILES: CCO[C@H]1CCN(Cc2c(OC)cc(C)c3[nH]ccc23)[C@H](c2ccc(C(=O)O)cc2)C1]

Iptacopan hydrochloride is chemically designated as 4-((2S,4S)-(4-ethoxy-1-((5-methoxy-7-methyl-JH-indol-4-yl)methyl)piperidin-2-yl))benzoic acid hydrochloride and can be represented by the following chemical structure:

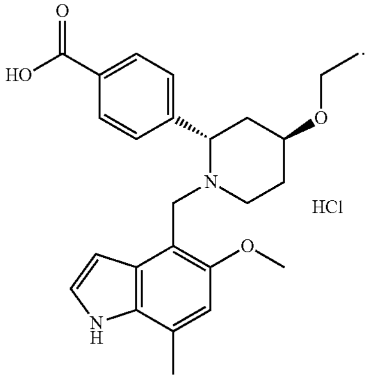 [SMILES: CCO[C@H]1CCN(Cc2c(OC)cc(C)c3[nH]ccc23)[C@H](c2ccc(C(=O)O)cc2)C1 ; Cl]

Iptacopan, iptacopan hydrochloride, and methods of preparation are disclosed in U.S. Pat. Nos. 9,682,968 and 10,093,663 (see Examples 26a, 26c and 26d), which are incorporated herein by reference in their entirety.

The form of iptacopan hydrochloride used as the investigational study drug for this study is a monohydrate (Form $H_B$) as shown in the formula below:

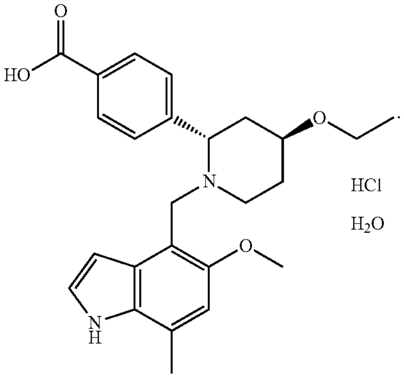 [SMILES: CCO[C@H]1CCN(Cc2c(OC)cc(C)c3[nH]ccc23)[C@H](c2ccc(C(=O)O)cc2)C1 ; Cl ; O]

(2S,4S)-2-(4-Carboxyphenyl)-4-ethoxy-1-[(5-methoxy-7-methyl-1H-indol-4-yl)methyl]piperidin-1-ium chloride-water (1/1)

Iptacopan hydrochloride monohydrate Form $H_B$ and methods for its preparation are disclosed in U.S. Ser. No. 63/026,637 and U.S. Ser. No. 63/052,699, published as WO 2021/234544, each of which is incorporated herein by reference in its entirety.

In one aspect, the disclosure provides a method for treating an autoimmune benign hematological disorder, e.g., immune thrombocytopenia (ITP), cold agglutinin disease (CAD), warm autoimmune hemolytic anemia (wAIHA), or thrombic thrombocytopenic purpura (TTP), in a subject, e.g., a patient, in need thereof, the method comprising orally administering to the subject, e.g., patient, iptacopan or a pharmaceutically acceptable salt thereof, e.g., iptacopan hydrochloride, at a therapeutically effective amount, to thereby treat the subject, e.g., patient.

In one aspect, the disclosure provides a method for treating an autoimmune benign hematological disorder, e.g., immune thrombocytopenia (ITP), cold agglutinin disease (CAD), warm autoimmune hemolytic anemia (wAIHA), or thrombic thrombocytopenic purpura (TTP), in a subject, e.g., a patient, in need thereof, the method comprising orally administering to the subject, e.g., patient, iptacopan or a pharmaceutically acceptable salt thereof, e.g., iptacopan hydrochloride, at about 50 mg to about 200 mg, about 50 mg, about 100 mg, or about 200 mg, to thereby treat the subject, e.g., patient (wherein the dosing amount refers to the anhydrous free base of iptacopan hydrochloride).

In one aspect, the disclosure provides a method for treating an autoimmune benign hematological disorder, e.g., immune thrombocytopenia (ITP), cold agglutinin disease (CAD), warm autoimmune hemolytic anemia (wAIHA), or thrombic thrombocytopenic purpura (TTP), in a subject, e.g., a patient, in need thereof, the method comprising orally administering to the subject, e.g., patient, iptacopan or a pharmaceutically acceptable salt thereof, e.g., iptacopan hydrochloride, once daily (q.d.), or twice daily (b.i.d.), e.g., about every 12 hours, to thereby treat the subject, e.g., patient (wherein the dosing amount refers to the anhydrous free base of iptacopan hydrochloride).

In one aspect, the disclosure provides a method for treating an autoimmune benign hematological disorder, e.g., immune thrombocytopenia (ITP), cold agglutinin disease (CAD), warm autoimmune hemolytic anemia (wAIHA), or thrombic thrombocytopenic purpura (TTP), in a subject, e.g., a patient, in need thereof, the method comprising orally administering to the subject, e.g., patient, iptacopan or a pharmaceutically acceptable salt thereof, e.g., iptacopan hydrochloride, every 2, 4, 6, 8, 10, 12, 14, 16, 20, or 24 hours, to thereby treat the subject, e.g., patient (wherein the dosing amount refers to the anhydrous free base of iptacopan hydrochloride).

In another aspect, the disclosure provides a method of assessing the efficacy of treatment of an autoimmune benign hematological disorder, e.g., immune thrombocytopenia (ITP), cold agglutinin disease (CAD), warm autoimmune hemolytic anemia (wAIHA), or thrombic thrombocytopenic purpura (TTP), in a subject, e.g., patient, treated with, or having been treated with iptacopan or a pharmaceutically acceptable salt thereof, e.g., iptacopan hydrochloride, the method comprising acquiring the level of a biomarker selected from the group consisting of (i) platelet count; (ii) hemoglobin level; (iii) Factor Bb level; (iv) Wieslab; (v) sC5b-9 level; (vi) C3/C4; and (vi') C4d level in the subject, e.g., patient, thereby assessing the efficacy of treatment. The method comprises acquiring at least one of any of (i) to (vi').

In an embodiment, the method further comprises acquiring the level of a second biomarker in the subject patient. In an embodiment, the second biomarker is selected from the group consisting of (vii) lactate dehydrogenase level; (viii) total bilirubin level; (ix) reticulocyte count; (x) haptoglobin level; (xi) anti-platelet antibody level; (xii) immature platelet fraction; (xiii) cold agglutinin titer; (xiv) total antiglobulin titer; and (xv) cold agglutinin thermal amplitude. The method comprises acquiring at least one of any of (vii) to (xv).

In another aspect, the disclosure provides iptacopan or a pharmaceutically acceptable salt thereof, e.g., iptacopan hydrochloride, for use in the treatment of an autoimmune benign hematological disorder, e.g., immune thrombocytopenia (ITP), cold agglutinin disease (CAD), warm autoimmune hemolytic anemia (wAIHA), or thrombic thrombocytopenic purpura (TTP), in a subject, e.g., a patient.

In another aspect, the disclosure provides use of iptacopan or a pharmaceutically acceptable salt thereof, e.g., iptacopan hydrochloride, in the manufacture of a medicament for the treatment of an autoimmune benign hematological disorder, e.g., immune thrombocytopenia (ITP), cold agglutinin disease (CAD), warm autoimmune hemolytic anemia (wAIHA), or thrombic thrombocytopenic purpura (TTP), in a subject, e.g., patient.

Treatment methods described herein can additionally comprise various evaluation steps prior to and/or following treatment with iptacopan or a pharmaceutically acceptable salt thereof, e.g. iptacopan hydrochloride. In an embodiment, prior to, during, and/or after administration of iptacopan or a pharmaceutically acceptable salt thereof, e.g. iptacopan hydrochloride, the methods further comprise the step of evaluating PK and PD parameters (e.g., plasma concentration of iptacopan or a pharmaceutically acceptable salt thereof, e.g. iptacopan hydrochloride. Evaluation may be achieved by sample analysis of bodily fluid, such as blood or plasma by e.g., mass spectroscopy, e.g. LC-MS.

BRIEF DESCRIPTION OF THE DRAWINGS

FIG. 2 is a table disclosing the assessment schedule during the initial phase of the treatment period (Part A).

FIG. 3 is a table disclosing the assessment schedule during the extension treatment period (Part B).

DETAILED DESCRIPTION

Figure 1:
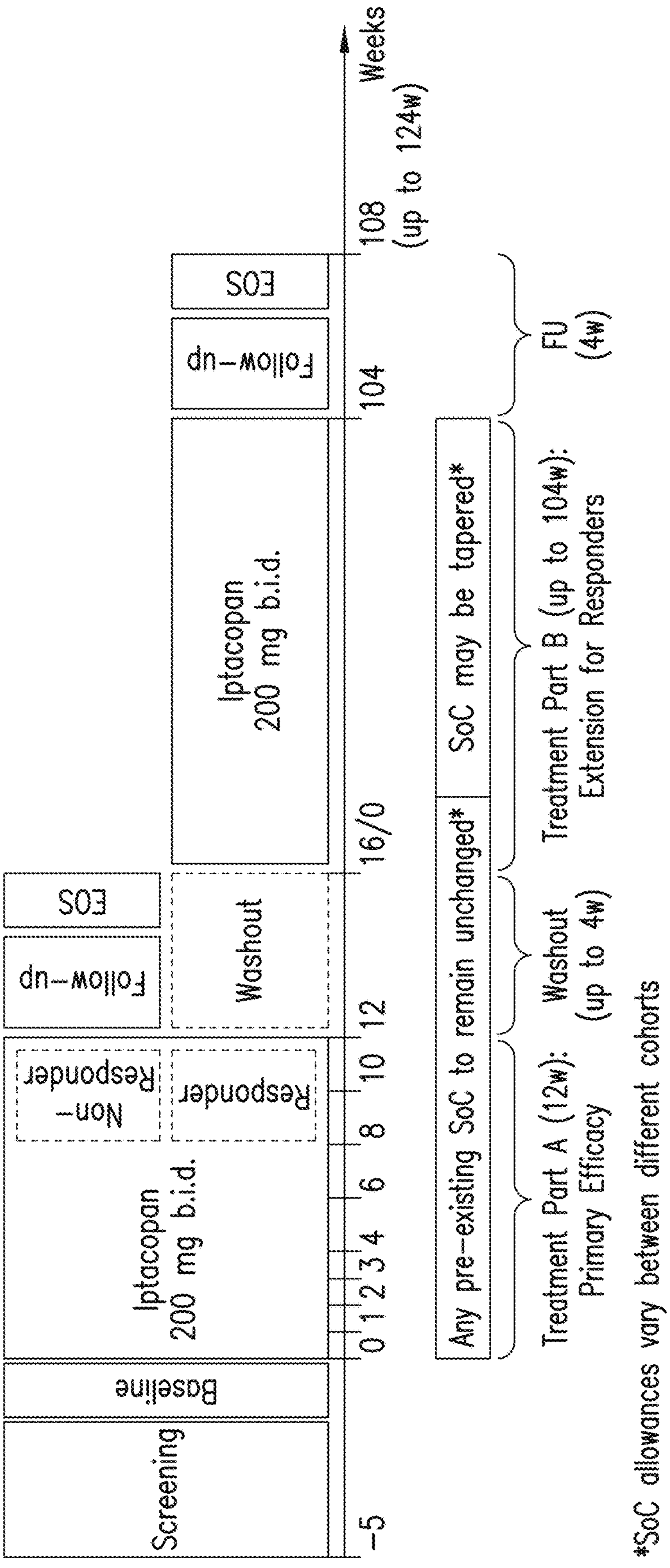
FIG. 1 depicts a schematic of the study design.

Described herein are a method of use, and a Phase 2 clinical study to determine safety and efficacy of iptacopan or a pharmaceutically acceptable salt thereof, e.g., iptacopan hydrochloride, in a subject having an autoimmune benign hematological disorder, such as immune thrombocytopenia (ITP), cold agglutinin disease (CAD), warm autoimmune hemolytic anemia (wAIHA), and thrombic thrombocytopenic purpura (TTP). The subjects may have exhibit high or low complement activation. In an embodiment, the subject has been previously treated, or is currently being treated, with at least one unique therapy administered with the intention to treat such autoimmune benign hematological disorder. The use and study described herein disclose the effects of iptacopan or a pharmaceutically acceptable salt thereof, e.g., iptacopan hydrochloride, on a range of efficacy assessments relevant to an autoimmune benign hematological disorder, including hematological parameters, anemia, hemolysis, as well as patient reported outcomes (PRO) for fatigue (Functional Assessment of Chronic Illness Therapy (FACIT)-fatigue) and quality of life.

In addition, this study will serve as a key trial for the development of iptacopan or a pharmaceutically acceptable salt thereof, e.g., iptacopan hydrochloride, as a treatment for patients with an autoimmune benign hematological disorder, such as ITP, CAD, wAIHA, and TTP. Accordingly, described herein are methods of treating an autoimmune benign hematological disorder, such as ITP, CAD, wAIHA, and TTP, in a subject in need thereof, the method comprising administering, e.g., orally, to the subject a dose, e.g., a once daily or twice daily dose, a therapeutically effective amount of iptacopan or a pharmaceutically acceptable salt thereof, e.g., iptacopan hydrochloride, e.g., at a dose of about 50 mg to about 200 mg, about 50 mg, about 100 mg, or about 200 mg (wherein the dosing amount refers to the anhydrous free base of iptacopan hydrochloride). Also described herein are methods of selecting the target patient population, methods of monitoring treatment of the target patient population, and methods of assessing safety and efficacy of treatment of the target patient population.

The details of the disclosure are set forth in the accompanying description below. Although methods and materials similar or equivalent to those described herein can be used in the practice or testing of the present disclosure, illustrative methods and materials are herein described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Remington's Pharmaceutical Sciences," Mack Publishing Co., Easton, Pa., 21st edition, 2005, which is hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "about" means within ±10% of a value.

As used herein, "administering" or "administration" means providing a pharmaceutical agent to an individual, and includes, but is not limited to, administering by a medical professional and self-administering. Administration of a pharmaceutical agent to an individual can be continuous, chronic, short or intermittent.

As used herein, the term "acquire" or "acquiring" as the terms are used herein, refer to obtaining possession of a physical entity (e.g., a sample, e.g., a blood sample or a blood plasma sample), or a value, e.g., a numerical value, by "directly acquiring" or "indirectly acquiring" the physical entity or value. "Directly acquiring" means performing a process (e.g., an analytical method) to obtain the physical entity or value. "Indirectly acquiring" refers to receiving the physical entity or value from another party or source (e.g., a third party laboratory that directly acquired the physical entity or value). Directly acquiring a value includes performing a process that includes a physical change in a sample or another substance, e.g., performing an analytical process which includes a physical change in a substance, e.g., a sample, performing an analytical method, e.g., a method as described herein, e.g., by sample analysis of bodily fluid, such as blood by, e.g., mass spectroscopy, e.g. LC-MS, e.g., LC-MS/MS methods.

As used herein, "dose" means a specified quantity of a pharmaceutical agent provided in a single administration, or in a specified time period. In certain embodiments, a dose can be administered in capsules. As used herein, the dosing amount refers to the anhydrous free base of iptacopan hydrochloride.

As used herein, "individual", "patient", "participant", or "subject" are used interchangeably and refer to an individual (e.g., a human) selected for treatment or therapy.

As used herein, "pharmaceutically acceptable salts" means physiologically and pharmaceutically acceptable salts of iptacopan, i.e., salts that retain the desired biological activity of iptacopan and do not impart undesired toxicological effects thereto. The term "pharmaceutically acceptable salt" or "salt" includes a salt prepared from pharmaceutically acceptable non-toxic acids or bases, including inorganic or organic acids and bases. "Pharmaceutically acceptable salts" of iptacopan may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Iptacopan hydrochloride and methods for its preparation are disclosed in U.S. Pat. Nos. 9,682,968 and 10,093,663 (see Example 26d), which is incorporated herein by reference in its entirety.

The term "hydrate" as used herein, refers to a crystalline solid where either water is cooperated in or accommodated by the crystal structure e.g., is part of the crystal structure or entrapped into the crystal (water inclusions). Thereby, water can be present in a stoichiometric or non-stoichiometric amount. When water is present in stoichiometric amount, the hydrate may be referred to by adding Greek numeral prefixes. For example, a hydrate may be referred to as a hemihydrate or as a monohydrate depending on the water/compound stoichiometry. The water content can be measured, for example, by Karl-Fischer-Coulometry.

The terms "anhydrous form" or "anhydrate" as used herein refer to a crystalline solid where no water is cooperated in or accommodated by the crystal structure. Anhydrous forms may still contain residual water, which is not part of the crystal structure but may be adsorbed on the surface or absorbed in disordered regions of the crystal. Typically, an anhydrous form does not contain more than 3.0 w-%, e.g., not more than 1.0 w-% of water, based on the weight of the crystalline form.

As used herein, the term "treat" means decrease, suppress, attenuate, diminish, arrest, or stabilize the development or progression of a disorder or disease, e.g., an autoimmune benign hematological disorder, such as ITP, CAD, wAIHA, and TTP.

As used herein, the term "unique prior therapy" means any pharmaceutical agent or type of non-pharmacological intervention (e.g., splenectomy, plasmapheresis) administered with the intention to treat the indications under study. Transfusions of blood products are not accounted as prior therapies. Any unique prior therapy will be counted once, even if it is stopped and restarted or given in different combinations. Different corticosteroids will be counted as a single unique prior therapy, whereas different members of other drug classes such as thrombopoietin receptor agonists will be counted as different unique prior therapies.

Unless otherwise specified, conventional definitions of terms control and conventional stable atom valences are presumed and achieved in all formulas and groups.

The articles "a" and "an" are used in this disclosure to refer to one or more than one (e.g., to at least one) of the grammatical object of the article. By way of example, "an element" means one element or more than one element.

Methods of Use

Autoimmune benign hematological disorders include a set of disorders that are characterized, inter alia, by the immune targeting and/or degradation of the host blood cells or hematological tissue. Exemplary autoimmune benign hematological disorders include immune thrombocytopenia (ITP), cold agglutinin disease (CAD), warm autoimmune hemolytic anemia (wAIHA), and thrombic thrombocytopenic purpura (TTP).

Provided herein is iptacopan or a pharmaceutically acceptable salt thereof, e.g., iptacopan hydrochloride, for use in the treatment of an autoimmune benign hematological disorder, e.g., ITP, CAD, wAIHA or TTP, in a subject, e.g., a patient, in need thereof, wherein the iptacopan or a pharmaceutically acceptable salt thereof, e.g., iptacopan hydrochloride, is to be orally administered at a therapeutically effective amount as described herein.

Provided herein is iptacopan or a pharmaceutically acceptable salt thereof, e.g., iptacopan hydrochloride, for treating an autoimmune benign hematological disorder, such as ITP, CAD, wAIHA and TTP, in a subject, e.g., a patient, in need thereof, wherein the iptacopan or a pharmaceutically acceptable salt thereof, e.g., iptacopan hydrochloride, is to be administered at a therapeutically effective amount as described herein.

Provided herein is a pharmaceutical composition comprising iptacopan or a pharmaceutically acceptable salt thereof, e.g., iptacopan hydrochloride, for use in the treatment of an autoimmune benign hematological disorder, e.g., ITP, CAD, wAIHA, or TTP, in a subject, e.g., a patient, in need thereof, wherein the iptacopan or a pharmaceutically acceptable salt thereof, e.g., iptacopan hydrochloride, is to be administered at a therapeutically effective amount as described herein.

Provided herein is a pharmaceutical composition comprising iptacopan or a pharmaceutically acceptable salt thereof. e.g., iptacopan hydrochloride, for treating an autoimmune benign hematological disorder, e.g., ITP, CAD, wAIHA, or TTP, in a subject, e.g., a patient, in need thereof, wherein the iptacopan or a pharmaceutically acceptable salt thereof, e.g., iptacopan hydrochloride, is to be administered at a therapeutically effective amount as described herein.

For simplicity, the description below where the term "iptacopan or a pharmaceutically acceptable salt thereof", "iptacopan hydrochloride", "iptacopan hydrochloride monohydrate", or "iptacopan hydrochloride monohydrate Form $H_B$" (collectively referred to as "an iptacopan entity") may also be substituted with the term "a pharmaceutical composition comprising [any of the aforementioned iptacopan entity]" where appropriate.

Provided herein is a method for treating an autoimmune benign hematological disorder, e.g., ITP, CAD, wAIHA or TTP, in a subject, e.g., a patient, in need thereof, the method comprising orally administering to the subject, e.g., patient, iptacopan or a pharmaceutically acceptable salt thereof, e.g., iptacopan hydrochloride, at a therapeutically effective amount, to thereby treat the subject, e.g., patient (wherein the dosing amount refers to the anhydrous free base of iptacopan hydrochloride).

In an embodiment, the method comprises orally administering iptacopan hydrochloride to the subject, e.g., patient. In an embodiment, the method comprises orally administering iptacopan hydrochloride monohydrate to the subject, e.g., patient. In an embodiment, the method comprises orally administering iptacopan hydrochloride monohydrate Form $H_B$ to the subject, e.g., patient.

In an embodiment, the method comprising orally administering to the subject, e.g., patient, iptacopan or a pharmaceutically acceptable salt thereof, e.g., iptacopan hydrochloride, at a therapeutically effective amount, e.g., a dose of about 50 mg to about 200 mg, about 50 mg, about 100 mg, or about 200 mg to thereby treat the subject, e.g., patient (wherein the dosing amount refers to the anhydrous free base of iptacopan hydrochloride).

In an embodiment, the method comprising orally administering to the subject, e.g., patient, iptacopan or a pharmaceutically acceptable salt thereof, e.g., iptacopan hydrochloride, at a therapeutically effective amount, once daily (q.d.) or twice daily (b.i.d.), to thereby treat the subject, e.g., patient (wherein the dosing amount refers to the anhydrous free base of iptacopan hydrochloride).

In an embodiment, the method comprising orally administering to the subject, e.g., patient, iptacopan or a pharmaceutically acceptable salt thereof, e.g., iptacopan hydrochloride, at a therapeutically effective amount, e.g., a dose of about 200 mg, e.g., twice daily (b.i.d.), e.g., about every 12 hours, to thereby treat the subject, e.g., patient (wherein the dosing amount refers to the anhydrous free base of iptacopan hydrochloride).

In an embodiment, the method comprising orally administering to the subject, e.g., patient, iptacopan or a pharmaceutically acceptable salt thereof, e.g., iptacopan hydrochloride, at a therapeutically effective amount, e.g., a dose of about 200 mg, e.g., once daily (q.d.), to thereby treat the subject, e.g., patient (wherein the dosing amount refers to the anhydrous free base of iptacopan hydrochloride).

In an embodiment, the method comprising orally administering to the subject, e.g., patient, iptacopan or a pharmaceutically acceptable salt thereof, e.g., iptacopan hydrochloride, at a therapeutically effective amount, e.g., a dose of about 100 mg, e.g., twice daily (b.i.d.), e.g., about every 12 hours, to thereby treat the subject, e.g., patient (wherein the dosing amount refers to the anhydrous free base of iptacopan hydrochloride).

In an embodiment, the method comprising orally administering to the subject, e.g., patient, iptacopan or a pharmaceutically acceptable salt thereof, e.g., iptacopan hydrochloride, at a therapeutically effective amount, e.g., a dose of about 100 mg, e.g., once daily (q.d.), to thereby treat the subject, e.g., patient (wherein the dosing amount refers to the anhydrous free base of iptacopan hydrochloride).

Provided herein is use of iptacopan or a pharmaceutically acceptable salt thereof, e.g., iptacopan hydrochloride, in the manufacture of a medicament for the treatment of an autoimmune benign hematological disorder, such as ITP, CAD, wAIHA and TTP, in a subject, e.g., a patient, in need thereof, wherein the medicament is to be administered orally to the subject, e.g., patient, at a therapeutically effective amount, e.g., about 50 mg to about 200 mg, about 50 mg, about 100 mg, or about 200 mg, e.g., once daily (q.d.) or twice daily (b.i.d.), e.g., about every 12 hours (wherein the dosing amount refers to the anhydrous free base of iptacopan hydrochloride).

Provided herein is use of iptacopan or a pharmaceutically acceptable salt thereof, e.g., iptacopan hydrochloride, in the treatment of an autoimmune benign hematological disorder, such as ITP, CAD, wAIHA and TTP, in a subject, e.g., a patient, in need thereof, wherein the iptacopan or a pharmaceutically acceptable salt thereof is to be administered orally to the subject, e.g., patient, at a therapeutically effective amount, e.g., about 50 mg to about 200 mg, about 50 mg, about 100 mg, or about 200 mg, e.g., once daily (q.d.) or twice daily (b.i.d.), e.g., about every 12 hours (wherein the dosing amount refers to the anhydrous free base of iptacopan hydrochloride).

Provided herein is use of iptacopan or a pharmaceutically acceptable salt thereof, e.g., iptacopan hydrochloride, for the treatment of an autoimmune benign hematological disorder, such as ITP, CAD, wAIHA and TTP, in a subject, e.g., a patient, in need thereof, wherein the iptacopan or a pharmaceutically acceptable salt thereof is to be administered orally to the subject, e.g., patient, at a therapeutically effective amount, e.g., about 50 mg to about 200 mg, about 50 mg, about 100 mg, or about 200 mg, e.g., once daily (q.d.) or twice daily (b.i.d.), e.g., about every 12 hours (wherein the dosing amount refers to the anhydrous free base of iptacopan hydrochloride).

The aspects of the disclosure above are further illustrated with the embodiments below which may be freely combined wherever appropriate. Some of the specific exemplified embodiments are also described hereinafter.

In an embodiment, the autoimmune benign hematological disorder is ITP, CAD, wAIHA or TTP.

In an embodiment, the immune thrombocytopenia (ITP) is primary ITP.

In an embodiment, the cold agglutinin disease (CAD) is primary CAD.

In an embodiment, the iptacopan or a pharmaceutically acceptable salt thereof is or is to be administered to the subject, e.g., patient.

In an embodiment, the iptacopan or a pharmaceutically acceptable salt thereof is or is to be administered orally to the subject, e.g., patient, at a dose of about 50 mg to about 200 mg (wherein the dosing amount refers to the anhydrous free base of iptacopan hydrochloride).

In an embodiment, the iptacopan or a pharmaceutically acceptable salt thereof is or is to be administered orally to the subject, e.g., patient, at a dose of about 50 mg (wherein the dosing amount refers to the anhydrous free base of iptacopan hydrochloride).

In an embodiment, the iptacopan or a pharmaceutically acceptable salt thereof is or is to be administered orally to the subject, e.g., patient, at a dose of about 100 mg (wherein the dosing amount refers to the anhydrous free base of iptacopan hydrochloride).

In an embodiment, the iptacopan or a pharmaceutically acceptable salt thereof is or is to be administered orally to the subject, e.g., patient, at a dose of about 200 mg (wherein the dosing amount refers to the anhydrous free base of iptacopan hydrochloride).

In an embodiment, the iptacopan or a pharmaceutically acceptable salt thereof is or is to be administered orally to the subject, e.g., patient, once daily.

In an embodiment, the iptacopan or a pharmaceutically acceptable salt thereof is or is to be administered orally to the subject, e.g., patient, twice daily, e.g., about every 12 hours (wherein the dosing amount refers to the anhydrous free base of iptacopan hydrochloride).

In an embodiment, the iptacopan or a pharmaceutically acceptable salt thereof is or is to be administered orally to the subject, e.g., patient, at a dose of 200 mg once daily.

In an embodiment, the iptacopan or a pharmaceutically acceptable salt thereof is or is to be administered orally to the subject, e.g., patient, at a dose of 200 mg twice daily, e.g., about every 12 hours (wherein the dosing amount refers to the anhydrous free base of iptacopan hydrochloride).

In an embodiment, the iptacopan or a pharmaceutically acceptable salt thereof is or is to be administered orally to the subject, e.g., patient, at a dose of 100 mg once daily.

In an embodiment, the iptacopan or a pharmaceutically acceptable salt thereof is or is to be administered orally to the subject, e.g., patient, at a dose of 100 mg twice daily, e.g., about every 12 hours (wherein the dosing amount refers to the anhydrous free base of iptacopan hydrochloride).

In an embodiment, the iptacopan or a pharmaceutically acceptable salt thereof is or is to be administered orally to the subject, e.g., patient, as monotherapy for treating the autoimmune benign hematological disorder.

In an embodiment, the iptacopan or a pharmaceutically acceptable salt thereof is or is to be administered orally to the subject, e.g., patient, as monotherapy for treating ITP.

In an embodiment, the iptacopan or a pharmaceutically acceptable salt thereof is or is to be administered orally to the subject, e.g., patient, as monotherapy for treating CAD.

In an embodiment, the iptacopan or a pharmaceutically acceptable salt thereof is or is to be administered orally to the subject, e.g., patient, as monotherapy for treating wAIHA.

In an embodiment, the iptacopan or a pharmaceutically acceptable salt thereof is or is to be administered orally to the subject, e.g., patient, as monotherapy for treating TTP.

In an embodiment, the iptacopan or a pharmaceutically acceptable salt thereof is or is to be administered orally to the subject, e.g., patient, for about 1 week, 2 weeks, 3 weeks, 4 weeks, 6 weeks, 8 weeks, 3 months, 4 months, 6 months, 8 months, 10 months, 12 months, 15 months, 18 months, 20 months, 24 months, 28 months, 32 months, or 36 months.

In an embodiment, the iptacopan or a pharmaceutically acceptable salt thereof is or is to be administered orally to the subject, e.g., patient, in combination with one or more additional agents for treating the autoimmune benign hematological disorder.

In an embodiment, the treating or treatment comprises orally administering iptacopan hydrochloride to the subject, e.g., patient.

In an embodiment, the treating or treatment comprises orally administering iptacopan hydrochloride monohydrate to the subject, e.g., patient.

In an embodiment, the treating or treatment comprises orally administering iptacopan hydrochloride monohydrate Form $H_B$ to the subject, e.g., patient.

In an embodiment, the method comprises orally administering iptacopan hydrochloride to the subject, e.g., patient.

In an embodiment, the method comprises orally administering iptacopan hydrochloride monohydrate to the subject, e.g., patient.

In an embodiment, the method comprises orally administering iptacopan hydrochloride monohydrate Form $H_B$ to the subject, e.g., patient.

In an embodiment, the iptacopan or a pharmaceutically acceptable salt thereof is or is to be administered orally is iptacopan hydrochloride.

In an embodiment, the iptacopan or a pharmaceutically acceptable salt thereof is or is to be administered orally is iptacopan hydrochloride monohydrate.

In an embodiment, the iptacopan or a pharmaceutically acceptable salt thereof is or is to be administered orally is iptacopan hydrochloride monohydrate Form $H_B$.

In an embodiment, the medicament to be administered orally comprises iptacopan hydrochloride.

In an embodiment, the medicament to be administered orally comprises iptacopan hydrochloride monohydrate.

In an embodiment, the medicament to be administered orally comprises iptacopan hydrochloride monohydrate Form $H_B$.

In an embodiment, the subject, e.g., patient, has or is diagnosed with having sustained thrombocytopenia or ongoing hemolysis.

In an embodiment, the subject, e.g., patient, has no evidence of or has not received a diagnosis of splenomegaly, hepatomegaly, or diffuse lymphadenopathy.

In an embodiment, the subject, e.g., patient, has no evidence of or has not received a diagnosis of a bacterial or viral infection (e.g., *Neisseria meningitidis, Steptococcus pneumonia*, or *Haemophilus influenzae* infection).

In an embodiment, the subject, e.g., patient, is 18 years of age or older.

In an embodiment, the subject, e.g., patient, has been previously treated with at least one unique prior treatment administered with the intention to treat an autoimmune benign hematological disorder, e.g., a treatment for ITP or CAD.

In an embodiment, the subject, e.g., patient, has been previously treated, or is currently being treated with at least one of a corticosteroid, an intravenous immunoglobulin (IVIG), an anti-Rho(D) immunoglobulin, and a thrombopoietin receptor agonist (TPO-RA).

In an embodiment, the subject, e.g., patient, has been previously treated, or is currently being treated with at least one of plasmapheresis, intravenous immunoglobulins (IVIG), rituximab, and bendamustine.

In an embodiment, the subject, e.g., patient, is naive to complement inhibitor therapy.

In an embodiment, the subject, e.g., patient, has not been previously treated with, or is not being treated with, a complement inhibitor therapy (e.g., an anti-C5 therapy), an immunosuppressive therapy (e.g., an immunosuppressive agent, such as, corticosteroids, mycophenolate mofetil (MMF), cyclophosphamide, or rituximab), or other therapy prescribed for an autoimmune benign hematological disorder, such as ITP, CAD, wAIHA and TTP.

In an embodiment, the subject, e.g., patient, has been previously treated, or is currently being treated, with a complement inhibitor therapy.

In an embodiment, the subject, e.g., patient, has been previously treated, or is currently being treated, with an anti-C5 therapy.

In an embodiment, the anti-C5 therapy is an anti-C5 monoclonal antibody therapy or a biosimilar thereof.

In an embodiment, the subject, e.g., patient, has been previously treated, or is currently being treated, with immunosuppressive therapy (e.g., an immunosuppressive agent, such as, corticosteroids, mycophenolate mofetil (MIF), cyclophosphamide, or rituximab), or other therapy prescribed for an autoimmune benign hematological disorder, e.g., ITP, CAD, wAIHA, or TTP.

In an embodiment, the subject, e.g., patient, has been previously treated, or is currently being treated with a thrombopoietin receptor agonist (TPO-RA).

In an embodiment, the subject, e.g., patient, for ITP, has been previously treated, or is currently being treated with a thrombopoietin receptor agonist (TPO-RA).

In an embodiment, the subject, e.g., patient, has been previously treated, or is currently being treated with a corticosteroid.

In an embodiment, the subject, e.g., patient, for ITP, has been previously treated, or is currently being treated with a corticosteroid.

In an embodiment, the subject, e.g., patient, has not been previously treated with, or is not being treated with, plasma exchange or plasma infusions (PE/PI). In an embodiment, the subject, e.g., patient, has not been previously treated with, or is not being treated with a medication selected from the group consisting of a targeted B-lymphocyte depleting therapy (e.g., rituximab), a systemic corticosteroid, an immunosuppressive or antineoplastic agent (e.g., Rho(D) IG, bendamustine, bortezomib, cyclosporine, cyclophosphamide, IVIG, mycophenolate mofetil, vincristine), an anti-thrombotic agent, an anti-platelet therapy, gemfibrozil, a CYP2C8 inhibitor (e.g., clopidogrel), and a substrate for the efflux transporter P-gp (e.g., digoxin, quinidine, paclitaxel, fentanyl, phenytoin).

In an embodiment, the subject, e.g., patient, has been vaccinated prior to administration of iptacopan or a pharmaceutically acceptable salt thereof, e.g. iptacopan hydrochloride.

In an embodiment, the subject, e.g., patient, has been vaccinated against one or more of *Neisseria meningitidis, Streptococcus pneumoniae*, and *Haemophilus influenzae* infections.

In an embodiment, the subject, e.g., patient, has been vaccinated at least one week or at least two weeks, three weeks, four weeks, or longer, prior to administration of iptacopan or a pharmaceutically acceptable salt thereof, e.g. iptacopan hydrochloride.

In an embodiment, the subject, e.g., patient, has, or is determined to have, a genetic mutation in components regulating the alternative complement pathway.

In an embodiment, the subject, e.g., patient, has or is determined to have a genetic mutation associated with an autoimmune benign hematological disorder, such as ITP or CAD.

In an embodiment, the subject, e.g., patient, has, or is determined to have, a genetic mutation selected from the group consisting of C3 (complement component 3), CD46 (cluster of differentiation 46), MCP (membrane cofactor protein), CFB (complement factor B), CFH (complement factor H), CFHR (complement factor H-related protein), and CFI (complement factor I).

In an embodiment, the subject, e.g., patient, does not have a co-morbidity, e.g., selected from the group consisting of severe kidney disease (e.g., CKD stage 4, dialysis), advanced cardiac disease (e.g., NYHA class IV), severe pulmonary arterial hypertension (e.g., WHO class IV), or has not experienced an unstable thrombotic event. In an embodiment, the subject, e.g., patient, does not have secondary immunodeficiency (including a positive HIV test result), or infection with Hepatitis B (HBV) or Hepatitis C (HCV). In an embodiment, the subject, e.g., patient, does not have a complement deficiency, e.g., an acquired or hereditary complement deficiency.

In an embodiment, the subject, e.g., patient, for ITP, has a platelet count that is about 30 k/μL or less, prior to treatment with iptacopan or a pharmaceutically acceptable salt thereof, e.g. iptacopan hydrochloride, e.g., during the screening period or prior to the start of the screen period.

In an embodiment, treating the subject, e.g., patient, for ITP, comprises achieving hematological normalization in platelet count, e.g., an increase in platelet levels compared to a reference standard (e.g., platelet levels in an untreated subject), e.g., greater than about 10 k/μL, 15 k/μL, 20 k/μL, 25 k/μL, 30 k/μL, 35 k/μL, 40 k/μL, 45 k/μL, 50 k/μL, 60 k/μL, 70 k/μL, 80 k/μL, 90 k/μL, 100 k/μL, or more. In an embodiment, the subject achieves an increase in platelet levels compared to a reference standard (e.g., platelet levels in an untreated subject), e.g., between about 10 k/μL and 100 k/μL, or about 25 k/μL to 75 k/μL, or about 30 to 60 k/μL. Relevant guidelines for establishing hematological normalization in platelet count are provided, e.g., in the ASH 2019 guidelines for ITP (Neunert et al (2019) *Blood Adv* 3(23): 3829-3866; Provan et al (2019) *Blood Adv*).

In an embodiment, treating the subject, e.g., patient, for ITP, comprises achieving an increase in platelet count, e.g. by at least 10 k/μL, 15 k/μL, 20 k/μL, 25 k/μL, 30 k/μL, 35 k/μL, 40 k/μL, 45 k/μL, 50 k/μL, 60 k/μL, 70 k/μL, 80 k/μL, 90 k/μL, or 100 k/μL, relative to prior to treatment.

In an embodiment, treating the subject, e.g., patient, for ITP, comprises achieving a platelet count of at least 50 k/μL, 60 k/μL, 70 k/μL, 80 k/μL, 90 k/μL, 100 k/μL, 110 k/μL, 120 k/μL, 130 k/μL, 140 k/μL, 150 k/μL, 180 k/μL, 200 k/μL, or 250 k/μL.

In an embodiment, treating the subject, e.g., patient, for ITP, comprises achieving a reduction in bleeding, e.g., an improvement of the modified WHO bleeding score, e.g., as defined by Kaufman et al. (Kaufman R M, Djulbegovic B, Gernsheimer T, et al (2015) Platelet transfusion: a clinical practice guideline from the AABB. Ann Intern Med; 162 (3):205-13), e.g., by 1, 2, 3, or 4, relative to prior to treatment.

In an embodiment, achieving an increase in platelet count comprises maintaining an increase in platelet count for at least about 1 week, for at least about 2 weeks, for at least about 3 weeks, for at least about 4 weeks, for at least about 5 weeks, for at least about 6 weeks, for at least about 7 weeks, for at least about 8 weeks, for at least about 9 weeks, or for at least about 10 weeks.

In an embodiment, hematological normalization in platelet count comprises maintaining platelet count for at least about 1 week, for at least about 2 weeks, for at least about 3 weeks, for at least about 4 weeks, for at least about 5 weeks, for at least about 6 weeks, for at least about 7 weeks, for at least about 8 weeks, for at least about 9 weeks, or for at least about 10 weeks.

In an embodiment, the subject, e.g., patient, has a platelet count (per microliter of blood) of less than about 150 k/μL prior to treatment with iptacopan or a pharmaceutically acceptable salt thereof, e.g., iptacopan hydrochloride. In an embodiment, the platelet count (per microliter of blood) is normalized after treatment with iptacopan or a pharmaceutically acceptable salt thereof, e.g., iptacopan hydrochloride, to about 150 k/μL or more, about 175 k/μL or more, about 200 k/μL or more, about 225 k/μL or more, about 250 k/μL or more, about 275 k/μL or more, about 300 k/μL or more, about 325 k/μL or more, about 350 k/μL or more, about 375 k/μL or more, about 400 k/μL or more, about 425 k/μL or more, about 450 k/μL or more. In an embodiment, the platelet count (per microliter of blood) is normalized after treatment with iptacopan or a pharmaceutically acceptable salt thereof, e.g., iptacopan hydrochloride, to a range of about 150 k/μL to about 450 k/μL.

In an embodiment, the subject, e.g., patient, for CAD, has a hemoglobin level that is about 10 g/dL or less, prior to treatment with iptacopan or a pharmaceutically acceptable salt thereof, e.g. iptacopan hydrochloride, e.g., during the screening period or prior to the start of the screen period.

In an embodiment, treating the subject, e.g., patient, for CAD comprises achieving hematological normalization in hemoglobin levels, e.g., an increase in hemoglobin level compared to a reference standard (e.g., hemoglobin levels in an untreated subject), e.g., by greater than about 0.5 g/dL, about 0.75 g/dL, about 1.0 g/dL, about 1.25 g/dL, about 1.5 g/dL, about 1.75 g/dL, about 2.0 g/dL, about 2.5 g/dL, about 3.0 g/dL, about 4.0 g/dL, about 5.0 g/dL, or more. In an embodiment, the subject achieves an increase in hemoglobin levels compared to a reference standard (e.g., hemoglobin levels in an untreated subject), e.g., by between about 0.1 g/dL and about 10 g/dL, or about 0.5 g/dL and about 5 g/dL, or about 0.5 g/dL and about 2.5 g/dL. Relevant guidelines for establishing hematological normalization in platelet count are provided, e.g., in relevant literature (Berentsen et al (2021) *Blood, p.* 1295-1303).

In an embodiment, treating the subject, e.g., patient, for CAD comprises achieving an increase in hemoglobin level, e.g., by at least 1.5 g/dL, 1.75 g/dL, 2.0 g/dL, 2.5 g/dL, 3.0 g/dL, 4.0 g/dL, or 5.0 g/dL, relative to prior to treatment.

In an embodiment, treating the subject, e.g., patient, for CAD comprises achieving a hemoglobin level of at least 10 g/dL, 11 g/dL, 12 g/dL, 13 g/dL 14 g/dL, or 15 g/dL. In an embodiment, treating the subject, e.g., patient, for CAD comprises achieving hematological normalization in hemoglobin levels, e.g., of at least 12 g/dL, 13 g/dL, 14 g/dL, 15 g/dL, 16 g/dL, or 17 g/dL.

In an embodiment, treating the subject, e.g., patient, for CAD comprises achieving a reduction in transfusion requirements relative to prior to treatment.

In an embodiment, achieving an increase in hemoglobin level comprises maintaining hemoglobin level for at least about 1 week, for at least about 2 weeks, for at least about 3 weeks, for at least about 4 weeks, for at least about 5 weeks, for at least about 6 weeks, for at least about 7 weeks, for at least about 8 weeks, for at least about 9 weeks, or for at least about 10 weeks.

In an embodiment, treating the subject, e.g., patient, comprises achieving a reduction in fatigue severity, e.g., by FACIT-Fatigue scale, relative to prior to treatment.

In an embodiment, treating the subject, e.g., patient, comprises achieving a tapering or a discontinuation of a background therapy, e.g., a thrombopoietin receptor agonist (TPO-RA) and a corticosteroid, relative to prior to treatment.

In an embodiment, the method comprises acquiring the level of (iii) Factor Bb; (iv) Wieslab; (v) sC5b-9; (vi) C3/C4; and (vi') C4d in the subject, e.g., patient. In an embodiment, the method comprises acquiring the level of (iii) Factor Bb. In an embodiment, the method comprises acquiring the level of (iv) Wieslab. In an embodiment, the method comprises acquiring the level of (v) sC5b-9 level. In an embodiment, the method comprises acquiring the level of (vi) C3/C4. In an embodiment, the method comprises acquiring the level of (vi') C4d.

In an embodiment, treating the subject, e.g., patient, comprises achieving a tapering of a background therapy, relative to prior to treatment.

In an embodiment, treating the subject, e.g., patient, comprises achieving a discontinuation of a background therapy.

In an embodiment, treating the subject, e.g., patient, comprises achieving a tapering of a thrombopoietin receptor agonist (TPO-RA), relative to prior to treatment.

In an embodiment, treating the subject, e.g., patient, comprises achieving a discontinuation of a thrombopoietin receptor agonist (TPO-RA).

In an embodiment, treating the subject, e.g., patient, comprises achieving a tapering of a corticosteroid, relative to prior to treatment.

In an embodiment, treating the subject, e.g., patient, comprises achieving a discontinuation of corticosteroid.

In an embodiment, the method further comprises acquiring the level of an additional biomarker in the subject patient. In an embodiment, the second biomarker is selected from the group consisting of (vii) lactate dehydrogenase (LDH) level; (viii) total bilirubin level; (ix) reticulocyte count; (x) haptoglobin level; (xi) anti-platelet antibody level (e.g., directed against GPIIb, GPIIIa, GPIIb/GPIIIa, or GPIbIX); (xii) immature platelet fraction; (xiii) cold agglutinin titer; (xiv) total antiglobulin titer; and (xv) cold agglutinin thermal amplitude. In an embodiment, the method further comprises acquiring (vii). In an embodiment, the method further comprises acquiring (viii). In an embodiment, the method further comprises acquiring (ix). In an embodiment, the method further comprises acquiring (x). In an embodiment, the method further comprises acquiring (xi). In an embodiment, the method further comprises acquiring (xii). In an embodiment, the method further comprises acquiring (xiii). In an embodiment, the method further comprises acquiring (xiv). In an embodiment, the method further comprises acquiring (xv). In an embodiment, the method further comprises acquiring two of (v)-(xv). In an embodiment, the method further comprises acquiring three of (v)-(xv). In an embodiment, the method further comprises acquiring four of (v)-(xv). In an embodiment, the method further comprises acquiring five of (v)-(xv). In an embodiment, the method further comprises acquiring six of (v)-(xv). In an embodiment, the method further comprises acquiring seven of (v)-(xv). In an embodiment, the method further comprises acquiring eight of (v)-(xv). In an embodiment, the method further comprises acquiring nine of (v)-(xv). In an embodiment, the method further comprises acquiring each of (v)-(xv). In an embodiment, the level of a biomarker in the subject, e.g., patient, is acquired by sample analysis of a bodily fluid, such as blood or plasma.

In an embodiment, the subject, e.g., patient, has an LDH level that is about 1.5 times or more of the upper limit of normal (ULN), prior to treatment with iptacopan or a pharmaceutically acceptable salt thereof, e.g. iptacopan hydrochloride, e.g., during the screening period or prior to the start of the screen period. In an embodiment, treating the subject, e.g., patient, comprises reducing the level of LDH in the subject, e.g., patient, e.g., as compared to baseline, e.g., as compared to the level of LDH in the subject prior to administration of iptacopan or a pharmaceutically acceptable salt thereof, e.g. iptacopan hydrochloride.

In an embodiment, the LDH level in the subject, e.g., patient, is reduced by at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, e.g., as compared to baseline, e.g., as compared to the level of LDH in the subject prior to administration of iptacopan or a pharmaceutically acceptable salt thereof, e.g. iptacopan hydrochloride. In an embodiment, the LDH level is reduced by at least about 30%, at least about 35%, at least about 40%, at least about 45%, at least about 50%, at least about 55%, at least about 60%, at least about 65%, or at least about 70%, e.g., as compared to baseline, e.g., as compared to the level of LDH in the subject prior to administration of iptacopan or a pharmaceutically acceptable salt thereof, e.g. iptacopan hydrochloride. In an embodiment, the LDH level in the subject, e.g., patient, is reduced by at least about 30% or 40%, e.g., as compared to baseline, e.g., as compared to the level of LDH in the subject prior to administration of iptacopan or a pharmaceutically acceptable salt thereof, e.g. iptacopan hydrochloride.

In an embodiment, treating the subject, e.g., patient, comprises improving kidney function.

In an embodiment, the subject, e.g., patient, has been, or is being treated with an immunosuppressive agent, such as a corticosteroid, mycophenolate mofetil (MMF), cyclophosphamide, or rituximab. Additional examples of immunosuppressive agents can be found in Bagga et al. (2019) *Pediatric Nephrology* 34:1465-1482.

In an embodiment, the subject, e.g., patient, has not been, or is not being treated with an immunosuppressive agent, such as a corticosteroid, mycophenolate mofetil (MMF), cyclophosphamide, or rituximab. In an embodiment, the subject, e.g., patient, has, or is determined to have, antibodies to complement Factor H.

In another aspect, the disclosure provides use of iptacopan or a pharmaceutically acceptable salt thereof, e.g., iptacopan hydrochloride, in the manufacture of a medicament for the treatment of autoimmune benign hematological disorder in a subject, e.g., a patient, wherein the medicament is to be administered orally to the subject, e.g., patient, at a dose of about 200 mg (wherein the dosing amount refers to the anhydrous free base of iptacopan hydrochloride). In an embodiment, the medicament is administered daily, e.g., twice daily, to the subject, e.g., patient.

In an embodiment, the medicament to be administered orally is iptacopan hydrochloride. In an embodiment, the medicament to be administered orally is iptacopan hydrochloride monohydrate. In an embodiment, the medicament to be administered orally is iptacopan hydrochloride monohydrate Form Ha.

In an embodiment, the subject, e.g., patient, has or is diagnosed as having high complement activity or low complement activity.

In another aspect, the disclosure provides iptacopan or a pharmaceutically acceptable salt thereof, e.g., iptacopan hydrochloride, for use in the treatment of an autoimmune benign hematological disorder in a subject, e.g., a patient. In an embodiment, the treatment comprises orally administering iptacopan or a pharmaceutically acceptable salt thereof, e.g., iptacopan hydrochloride, at a dose of about 200 mg (wherein the dosing amount refers to the anhydrous free base of iptacopan hydrochloride). In an embodiment, the treatment comprises orally administering iptacopan or a pharmaceutically acceptable salt thereof, e.g., iptacopan hydrochloride, at a dose of about 200 mg twice daily (b.i.d.) (wherein the dosing amount refers to the anhydrous free base of iptacopan hydrochloride). In an embodiment, the treatment comprises administering iptacopan or a pharmaceutically acceptable salt thereof, e.g., iptacopan hydrochloride to the subject, e.g., patient, every 2, 4, 6, 8, 10, 12, 14, 16, 20, or 24 hours. In an embodiment, iptacopan is administered to the subject, e.g., patient, for about 1 week, 2 weeks, 3 weeks, 4 weeks, 6 weeks, 8 weeks, 3 months, 4 months, 6 months, 8 months, 10 months, 12 months, 15 months, 18 months, 20 months, 24 months, 28 months, 32 months, or 36 months.

Patient Selection and Monitoring

As an example of the disclosed method, the Phase 2 study will enroll subjects diagnosed with an autoimmune benign hematological disorder with evidence of complement activation in at least a subset of subjects. The study is designed as an adaptive basket study with two initial cohorts, namely ITP and CAD. The study may be amended to include additional cohorts, including subjects diagnosed with warm autoimmune hemolytic anemia (wAIHA) and/or thrombotic thrombocytopenic purpura (TTP).

In the primary ITP cohort, subjects will have or be diagnosed with ITP and sustained thrombocytopenia.

In the primary CAD cohort, subjects will have or be diagnosed with having CAD, sustained anemia, and evidence of hemolysis.

Genetic testing will be done for a selected set of genes known to be involved in autoimmune benign hematological disorder (e.g., ITP or CAD) etiology, as it provides important prognostic information such as study treatment response, relapse and recurrence after transplantation. However, this specific genetic analysis will not be part of the screening process or determining eligibility. Additional assessments will include assessment of related biomarkers (such as platelet count, hemoglobin, Factor Bb, Wieslab, sC5b-9, and C3/C4) and autoantibodies to complement proteins (such as factor H autoantibodies). Once clinical diagnosis of ITP or CAD is confirmed by the investigator, genetic and biomarkers/auto-antibody testing will be performed wherever permitted per local regulations and after specific consent has been obtained from the patient.

Iptacopan or a pharmaceutically acceptable salt thereof, e.g., iptacopan hydrochloride, can inhibit complement activation. Accordingly, a subject, e.g., a patient, can be selected for treatment with iptacopan or a pharmaceutically acceptable salt thereof, e.g., iptacopan hydrochloride, by first evaluating the patient to determine whether the subject, e.g., patient, has evidence of an autoimmune benign hematological disorder (e.g., ITP or CAD), e.g., low platelet count ($<150\times10^9$/L), hemolytic anemia (LDH$\geq$1.5$\times$ULN, hemoglobin$\leq$LLN), and optionally administering to the subject, e.g., patient, iptacopan or a pharmaceutically acceptable salt thereof, e.g., iptacopan hydrochloride.

In an embodiment, the subject, e.g., patient, can be monitored by evaluating certain PK/PD parameters, such as the level of iptacopan or a pharmaceutically acceptable salt thereof, e.g., iptacopan hydrochloride, the level of platelets and/or the level of hemoglobin.

Efficacy Assessment

The primary efficacy assessment to determine successful treatment of an autoimmune benign hematological disorder comprises an assessment of subject platelet count or hemoglobin levels without the use of exogenous rescue therapy. Accordingly, provided herein a method of assessing the efficacy of treatment in a subject, e.g., patient, treated with, or having been treated with, iptacopan or a pharmaceutically acceptable salt thereof, e.g. iptacopan hydrochloride at a dose of about 200 mg, e.g., twice daily (b.i.d.), the method comprising assessing the change in the platelet count or hemoglobin level in a subject, e.g., without the use of exogenous rescue therapy, in the subject, to assess the efficacy of treatment.

In an embodiment, the subject has or is diagnosed with having ITP. In an embodiment, assessing the efficacy of a subject having or diagnosed as having ITP comprises assessing the change in the platelet count of the subject. In an embodiment, the subject has or is diagnosed with having CAD. In an embodiment, assessing the efficacy of a subject having or diagnosed as having CAD comprises assessing the change in the hemoglobin levels of the subject.

In another aspect, the disclosure provides a method of assessing the efficacy of treatment in a population of patients treated with, or having been treated with, iptacopan or a pharmaceutically acceptable salt thereof, e.g. iptacopan hydrochloride at a dose of about 200 mg twice daily (b.i.d.), the method comprising determining the percentage of the population of patients achieving a selected outcome, to assess efficacy of treatment (wherein the dosing amount refers to the anhydrous free base of iptacopan hydrochloride).

In an embodiment, the percentage of the population of patients achieving a selected outcome is about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, or about 95% or more. In an embodiment, the percentage of the population of patients achieving a selected outcome is from about 30% to about 70%.

In an embodiment, achieving a selected outcome comprises achieving a platelet count of greater than about 10 k/μL, 15 k/μL, 20 k/μL, 25 k/μL, 30 k/μL, 35 k/μL, 40 k/μL, 45 k/μL, 50 k/μL, 60 k/μL, 70 k/μL, 80 k/μL, 90 k/μL, 100 k/μL, or more. In an embodiment, the subject achieves an increase in platelet levels compared to a reference standard (e.g., platelet levels in an untreated subject), e.g., between about 10 k/μL and 100 k/μL, or about 25 k/μL to 75 k/μL, or about 30 to 60 k/μL. In an embodiment, achieving a selected outcome comprises achieving a platelet count of greater than 50 k/μL.

In an embodiment, the platelet count (per liter of blood) is normalized after treatment with iptacopan or a pharmaceutically acceptable salt thereof, e.g., iptacopan hydrochloride, to about 150 k/μL or more, about 175 k/μL or more, about 200 k/μL or more, about 225 k/μL or more, about 250 k/μL or more, about 275 k/μL or more, about 300 k/μL or more, about 325 k/μL or more, about 350 k/μL or more, about 375 k/μL or more, about 400 k/μL or more, about 425 k/μL or more, about 450 k/μL or more, e.g., normalized to a range of about 150 k/μL to about 450 k/μL.

In an embodiment, achieving a selected outcome, e.g., an increase in platelet count, comprises maintaining platelet count for at least about 1 week, for at least about 2 weeks, for at least about 3 weeks, for at least about 4 weeks, for at least about 5 weeks, for at least about 6 weeks, for at least about 7 weeks, for at least about 8 weeks, for at least about 9 weeks, or for at least about 10 weeks.

In an embodiment, achieving a selected outcome comprises achieving an increase in hemoglobin levels, e.g., an increase in hemoglobin level compared to a reference standard (e.g., hemoglobin levels in an untreated subject), e.g., greater than about 0.5 g/dL, 0.75 g/dL, 1.0 g/dL, 1.25 g/dL, 1.5 g/dL, 1.75 g/dL, 2.0 g/dL, 2.5 g/dL, 3.0 g/dL, 4.0 g/dL, 5.0 g/dL, or more. In an embodiment, the subject achieves an increase in hemoglobin levels compared to a reference standard (e.g., hemoglobin levels in an untreated subject), e.g., between about 0.1 g/dL and about 10 g/dL, or about 0.5 g/dL and 5 g/dL, or about 0.5 g/dL and 2.5 g/dL. In an embodiment, achieving a selected outcome comprises achieving an increase in hemoglobin levels in a subject greater than or equal to 1.5 g/dL.

In an embodiment, achieving a selected outcome, e.g., an increase in hemoglobin levels, comprises maintaining hemoglobin levels for at least about 1 week, for at least about 2 weeks, for at least about 3 weeks, for at least about 4 weeks, for at least about 5 weeks, for at least about 6 weeks, for at least about 7 weeks, for at least about 8 weeks, for at least about 9 weeks, or for at least about 10 weeks.

In an embodiment, the selected outcome comprises a normalization of levels of a biomarker selected from the group consisting of Factor Bb, Wieslab; sC5b-9, C3/C4, total bilirubin, reticulocyte count, haptoglobin, anti-platelet antibody level (e.g., directed against GPIIb, GPIIIa, GPIIb/GPIIIa, or GPIbIX), immature platelet fraction, cold agglutinin titer, total antiglobulin titer; and cold agglutinin thermal amplitude.

In an embodiment, the level of LDH is below ULN (upper limit of normal).

In another aspect, the disclosure provides a method of assessing the efficacy of treatment in a population of patients treated with, or having been treated with, iptacopan or a pharmaceutically acceptable salt thereof, e.g. iptacopan hydrochloride at a dose of about 200 mg twice daily (b.i.d.), the method comprising determining the percentage of the population of patients achieving an increase in platelet count of about 1.0, 1.5, or 2.0 g/dL or more, e.g., as compared to baseline, e.g., as compared to hemoglobin levels in the patient population prior to treatment with iptacopan or a pharmaceutically acceptable salt thereof, e.g. iptacopan hydrochloride, to assess efficacy of treatment (wherein the dosing amount refers to the anhydrous free base of iptacopan hydrochloride).

In an embodiment, the percentage of the population of patients achieving an increase in platelet count is about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, or about 95% or more.

In another aspect, the disclosure provides a method of assessing the efficacy of treatment in a population of patients treated with, or having been treated with, iptacopan or a pharmaceutically acceptable salt thereof, e.g. iptacopan hydrochloride at a dose of about 200 mg twice daily (b.i.d.), the method comprising determining the percentage of the population of patients achieving an increase in hemoglobin levels of about 25, 50, or 100 k/μL or more, e.g., as compared to baseline, e.g., as compared to platelet count in the patient population prior to treatment with iptacopan or a pharmaceutically acceptable salt thereof, e.g. iptacopan hydrochloride, to assess efficacy of treatment (wherein the dosing amount refers to the anhydrous free base of iptacopan hydrochloride).

In an embodiment, the percentage of the population of patients achieving an increase in hemoglobin levels is about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, or about 95% or more.

SPECIFIC EMBODIMENTS

While various specific embodiments have been illustrated and described, it will be appreciated that various changes can be made without departing from the spirit and scope of the disclosure(s). The present disclosure is exemplified by the numbered embodiments set forth below.

1. A method of treating an autoimmune hematological disorder in a subject, e.g., a patient, in need thereof, the method comprising administering orally to the subject, e.g., the patient, a therapeutically effective amount of iptacopan or a pharmaceutically acceptable salt thereof (e.g., iptacopan hydrochloride) to thereby treat the subject, e.g. patient.

2. The method of embodiment 1, wherein the autoimmune hematological disorder is selected from the group consisting of immune thrombocytopenia (ITP), cold agglutinin disease (CAD). warm autoimmune hemolytic anemia (wAIHA), and thrombic thrombocytopenic purpura (TTP).

3. The method of embodiments 1 or 2, wherein the autoimmune hematological disorder is immune thrombocytopenia (ITP).

4. The method of embodiments 1 or 2, wherein the autoimmune hematological disorder is cold agglutinin disease (CAD).

5. The method of any one of embodiments 1 to 4, comprising administering orally to the subject, e.g., the patient, a therapeutically effective amount of iptacopan or a pharmaceutically acceptable salt thereof (e.g., iptacopan hydrochloride) to thereby treat the subject, e.g. patient.

6. The method of any one of embodiments 1 to 5, wherein the therapeutically effective amount of iptacopan or a pharmaceutically acceptable salt thereof (e.g., iptacopan hydrochloride) comprises a dose of about 50 mg to about 200 mg, about 50 mg, about 100 mg, or about 200 mg (wherein the dosing amount refers to the anhydrous free base of iptacopan hydrochloride).

7. The method of any one of embodiments 1 to 6, wherein the therapeutically effective amount of iptacopan or a pharmaceutically acceptable salt thereof (e.g., iptacopan hydrochloride) is administered once daily (q.d.) or twice daily (b.i.d.) to the subject, e.g., the patient.

8. The method of any one of embodiments 1 to 7, wherein the therapeutically effective amount of iptacopan or a pharmaceutically acceptable salt thereof (e.g., iptacopan hydrochloride) is administered for at least 6 weeks, 8 weeks, 10 weeks, 12 weeks, 14 weeks, 16 weeks or longer to the subject, e.g., the patient.

9. The method of any one of embodiments 1 to 8, wherein the method comprises orally administering iptacopan or a pharmaceutically acceptable salt thereof (e.g., iptacopan hydrochloride) to the subject, e.g., the patient.

10. The method of any one of embodiments 1 to 9, wherein the method comprises orally administering iptacopan hydrochloride monohydrate (e.g., iptacopan hydrochloride monohydrate Form $H_B$) to the subject, e.g., the patient.

11. The method of any one of embodiments 1 to 10, wherein the subject, e.g., patient, has not been previously treated with a complement inhibitor therapy.

12. The method of any one of embodiments 1 to 11, wherein the subject, e.g., patient, has not been previously treated with, or is not being treated with, an anti-C5 therapy, immunosuppressive therapy (e.g., an immunosuppressive agent), or other therapy prescribed for an autoimmune hematological condition, e.g., ITP or CAD.

13. The method of any one of embodiments 1 to 10, wherein the subject, e.g., patient, has been previously treated, or is currently being treated, with a complement inhibitor therapy.

14. The method of embodiment 13, wherein the subject, e.g., patient, has been previously treated, or is currently being treated, with an anti-C5 therapy.

15. The method of any one of embodiments 1 to 14, wherein the subject, e.g., patient, has a sC5b-9 level of greater than or equal to 200 ng/mL.

16. The method of any one of embodiments 1 to 14, wherein the subject, e.g., patient, has a sC5b-9 level of less than 200 ng/mL.

17. The method of any one of embodiments 1 to 16, wherein the autoimmune benign hematological disorder is selected from the group consisting of warm autoimmune hemolytic anemia (wAIHA) and thrombotic thrombocytopenic purpura (TTP).

18. The method of any one of embodiments 1 to 17, wherein the subject, e.g., patient, has been vaccinated prior to administration of iptacopan or a pharmaceutically acceptable salt thereof, e.g. iptacopan hydrochloride.

19. The method of any one of embodiments 1 to 18, wherein the subject, e.g., patient, has been vaccinated against one or more of *Neisseria meningitidis, Streptococcus pneumoniae*, and *Haemophilus influenzae* infections.

20. The method of any one of embodiments 1 to 19, wherein the subject, e.g., patient, has been vaccinated at least one week or at least two weeks, e.g., about 14 days, prior to administration of iptacopan or a pharmaceutically acceptable salt thereof, e.g. iptacopan hydrochloride.

21. The method of any one of embodiments 1 to 20, wherein the subject, e.g., patient, is receiving antibiotic therapy, e.g., prophylactic antibiotic therapy.

22. The method of any one of embodiments 1 to 21, wherein the subject, e.g., patient, has been previously treated, or is currently being treated with at least one unique prior treatment administered with the intention to treat an autoimmune benign hematological disorder.

23. The method of any one of embodiments 1 to 22, wherein the subject, e.g., patient, has been previously treated, or is currently being treated with at least one of a corticosteroid, an intravenous immunoglobulin (IVIG), an anti-Rho(D) immunoglobulin, and a thrombopoietin receptor agonist (TPO-RA).

24. The method of any one of embodiments 1 to 23, wherein the subject, e.g., patient, for ITP, has been previously treated, or is currently being treated with at least one of a corticosteroid, an intravenous immunoglobulin (IVIG), an anti-Rho(D) immunoglobulin, and a thrombopoietin receptor agonist (TPO-RA).

25. The method of any one of embodiments 1 to 24, wherein the subject, e.g., patient, has been previously treated, or is currently being treated with at least one of plasmapheresis, intravenous immunoglobulins (IVIG), rituximab, and bendamustine.

26. The method of any one of embodiments 1 to 25, wherein the subject, e.g., patient, for CAD, has been previously treated, or is currently being treated with at least one of plasmapheresis, intravenous immunoglobulins (IG), rituximab, and bendamustine.

27. The method of any one of embodiments 1 to 26, wherein treating comprises an increase in platelet count in the subject, e.g., greater than about 10 k/μL, 15 k/μL, 20 k/μL, 25 k/μL, 30 k/μL, 35 k/μL, 40 k/μL, 45 k/μL, 50 k/μL, 60 k/μL, 70 k/μL, 80 k/μL, 90 k/μL, 100 k/μL, or more, compared to a reference standard (e.g., an untreated subject).

28. The method of any one of embodiments 1 to 27, wherein treating comprises achieving an increase in platelet count, e.g. by at least 10 k/μL, 15 k/μL, 20 k/μL, 25 k/μL, 30 k/μL, 35 k/μL, 40 k/μL, 45 k/μL, 50 k/μL, 60 k/μL, 70 k/μL, 80 k/μL, 90 k/μL, or 100 k/μL, relative to prior to treatment.

29. The method of any one of embodiments 1 to 28, wherein treating comprises achieving a platelet count of at least 50 k/μL, 60 k/μL, 70 k/μL, 80 k/μL, 90 k/μL, 100 k/μL, 110 k/μL, 120 k/μL, 130 k/μL, 140 k/μL, 150 k/μL, 180 k/μL, 200 k/μL, or 250 k/μL.

30. The method of any one of embodiments 1 to 29, wherein treating comprises achieving a reduction in bleeding, e.g., an improvement of the modified WHO bleeding score, e.g., as defined by Kaufman et al. (Kaufman R M, Djulbegovic B, Gernsheimer T, et al (2015) Platelet transfusion: a clinical practice guideline from the AABB. Ann Intern Med; 162(3):205-13), e.g., by 1, 2, 3, or 4, relative to prior to treatment.

31. The method of any one of embodiments 1 to 30, wherein treating comprises maintaining an increase in platelet count for at least about 1 week, for at least about 2 weeks, for at least about 3 weeks, for at least about 4 weeks, for at least about 5 weeks, for at least about 6 weeks, for at least about 7 weeks, for at least about 8 weeks, for at least about 9 weeks, or for at least about 10 weeks.

32. The method of any one of embodiments 1 to 31, wherein the increase in platelet count comprises maintaining platelet count for at least about 1 week, for at least about 2 weeks, for at least about 3 weeks, for at least about 4 weeks, for at least about 5 weeks, for at least about 6 weeks, for at least about 7 weeks, for at least about 8 weeks, for at least about 9 weeks, or for at least about 10 weeks.

33. The method of any one of embodiments 1 to 32, wherein the subject, e.g., patient, has a platelet count (per liter of blood) of less than about 150 k/μL prior to treatment with iptacopan or a pharmaceutically acceptable salt thereof, e.g., iptacopan hydrochloride.

34. The method of any one of embodiments 1 to 33, wherein the platelet count (per microliter of blood) is normalized after treatment with iptacopan or a pharmaceutically acceptable salt thereof, e.g., iptacopan hydrochloride, to about 150 k/μL or more, about 175 k/μL or more, about 200 k/μL or more, about 225 k/μL or more, about 250 k/μL or more, about 275 k/μL or more, about 300 k/μL or more, about 325 k/μL or more, about 350 k/μL or more, about 375 k/μL or more, about 400 k/μL or more, about 425 k/μL or more, about 450 k/μL or more, e.g., normalized to a range of about 150 k/μL to about 450 k/μL.

35. The method of any one of embodiments 1 to 34, the subject, e.g., patient, for CAD, has a hemoglobin level that is about 10 g/dL or less, prior to treatment with iptacopan or a pharmaceutically acceptable salt thereof, e.g. iptacopan hydrochloride, e.g., during the screening period or prior to the start of the screen period.

36. The method of embodiment 35, wherein treating comprises an increase in hemoglobin levels in the subject, e.g., greater than about 0.5 g/dL, 0.75 g/dL, 1.0 g/dL, 1.25 g/dL, 1.5 g/dL, 1.75 g/dL, 2.0 g/dL, 2.5 g/dL, 3.0 g/dL, 4.0 g/dL, 5.0 g/dL, or more, compared to a reference standard (e.g., an untreated subject).

37. The method of embodiment 35 or 36, wherein treating the subject, e.g., patient, comprises increasing the hemoglobin level in the subject, e.g., patient, e.g., by about 0.2 g/dL or more, by about 0.3 g/dL or more, by about 0.4 g/dL or more, by about 0.5 g/dL or more, by about 0.75 g/dL or more, by about 1 g/dL or more, by about 1.25 g/dL or more, by about 1.5 g/dL or more, by about 1.75 g/dL or more, by about 2 g/dL or more, by about 2.25 g/dL or more, about 2.5 g/dL or more, by about 2.75 g/dL or more, or about 3 g/dL or more, e.g., about 2 g/dL or more, e.g., as compared to baseline, e.g., as compared to the hemoglobin level in the subject, e.g., patient, prior to treatment with iptacopan or a pharmaceutically acceptable salt thereof, e.g., iptacopan hydrochloride.

38. The method of any one of embodiments 35 to 37, wherein treating comprises achieving hematological normalization in hemoglobin levels, e.g., an increase in hemoglobin level compared to a reference standard (e.g., hemoglobin levels in an untreated subject), e.g., by greater than about 0.5 g/dL, about 0.75 g/dL, about 1.0 g/dL, about 1.25 g/dL, about 1.5 g/dL, about 1.75 g/dL, about 2.0 g/dL, about 2.5 g/dL, about 3.0 g/dL, about 4.0 g/dL, about 5.0 g/dL, or more. In an embodiment, the subject achieves an increase in hemoglobin levels compared to a reference standard (e.g., hemoglobin levels in an untreated subject), e.g., by between about 0.1 g/dL and about 10 g/dL, or about 0.5 g/dL and about 5 g/dL, or about 0.5 g/dL and about 2.5 g/dL.

39. The method of any one of embodiments 35 to 38, wherein treating comprises achieving an increase in hemoglobin level, e.g., by at least 1.5 g/dL, 1.75 g/dL, 2.0 g/dL, 2.5 g/dL, 3.0 g/dL, 4.0 g/dL, or 5.0 g/dL, relative to prior to treatment.

40. The method of any one of embodiments 35 to 39, wherein treating comprises achieving a hemoglobin level of at least 10 g/dL, 11 g/dL, 12 g/dL, 13 g/dL 14 g/dL, or 15 g/dL.

41. The method of any one of embodiments 35 to 40, wherein treating comprises achieving hematological normalization in hemoglobin levels of at least 12 g/dL, 13 g/dL, 14 g/dL, 15 g/dL, 16 g/dL, or 17 g/dL.

42. The method of any one of embodiments 35 to 41, wherein treating comprises achieving a reduction in transfusion requirements relative to prior to treatment.

43. The method of any one of embodiments 35 to 42, wherein treating comprises maintaining hemoglobin level for at least about 1 week, for at least about 2 weeks, for at least about 3 weeks, for at least about 4 weeks, for at least about 5 weeks, for at least about 6 weeks, for at least about 7 weeks, for at least about 8 weeks, for at least about 9 weeks, or for at least about 10 weeks.

44. The method of any one of embodiments 1 to 43, wherein the method further comprises assessing the level of a biomarker selected from the group consisting of Factor Bb; Wieslab; sC5b-9; and C3/C4 in the subject, e.g., patient.

45. The method of any one of embodiments 1 to 44, wherein the method further comprises assessing the level of a biomarker selected from the group consisting of lactate dehydrogenase (LDH); total bilirubin; reticulocyte count; haptoglobin; anti-platelet antibody level (e.g., directed against GPIIb, GPIIIa, GPIIb/GPIIIa, or GPIbIX); immature platelet fraction; cold agglutinin titer; total antiglobulin titer; and cold agglutinin thermal amplitude.

46. The method of any one of embodiments 1 to 45, wherein the platelet level, hemoglobin level, or level of another biomarker in the subject, e.g., patient, is acquired by sample analysis.

47. The method of any one of embodiments 1 to 46, wherein treating comprises achieving a reduction in fatigue severity, e.g., by FACIT-Fatigue scale, relative to prior to treatment.

48. The method of any one of embodiments 1 to 47, wherein treating comprises achieving a tapering or a discontinuation of a background therapy, e.g., a thrombopoietin receptor agonist (TPO-RA) and a corticosteroid, relative to prior to treatment.

49. A method of treating immune thrombocytopenia (ITP) in a subject, e.g., a patient, in need thereof, the method comprising administering orally, to the subject, e.g., the patient, a pharmaceutically effective amount of iptacopan or a pharmaceutically acceptable salt thereof (e.g., iptacopan hydrochloride), e.g., at a dose of about 200 mg, to thereby treat the subject, e.g. patient (wherein the dosing amount refers to the anhydrous free base of iptacopan hydrochloride).

50. The method of embodiment 49, wherein iptacopan or a pharmaceutically acceptable salt thereof (e.g., iptacopan hydrochloride) is administered orally to the subject at a dose of about 200 mg twice daily (b.i.d.).

51. The method of embodiment 49 or 50, wherein iptacopan or a pharmaceutically acceptable salt thereof (e.g., iptacopan hydrochloride) is administered twice daily (b.i.d.) to the subject, e.g., the patient.

52. The method of any one of embodiments 49 to 51, wherein iptacopan or a pharmaceutically acceptable salt thereof (e.g., iptacopan hydrochloride) is administered twice daily (b.i.d.) for at least 12 weeks to the subject, e.g., the patient.

53. The method of any one of embodiments 49 to 52, wherein the method comprises orally administering iptacopan hydrochloride (e.g., iptacopan hydrochloride monohydrate) to the subject, e.g., the patient.

54. The method of any one of embodiments 49 to 53, wherein the method comprises orally administering iptacopan hydrochloride monohydrate (e.g., iptacopan hydrochloride monohydrate Form $H_B$) to the subject, e.g., the patient.

55. The method of any one of embodiments 49 to 54, wherein the subject, e.g., patient, has or is diagnosed with having thrombocytopenia.

56. The method of any one of embodiments 49 to 55, wherein the subject, e.g., patient, has a sC5b-9 level of greater than or equal to 200 ng/mL.

57. The method of any one of embodiments 49 to 55, wherein the subject, e.g., patient, has a sC5b-9 level of less than 200 ng/mL.

58. The method of any one of embodiments 49 to 57, wherein treating comprises an increase in platelet count in the subject, e.g., by greater than about 10 k/μL, 15 k/μL, 20 k/μL, 25 k/μL, 30 k/μL, 35 k/μL, 40 k/μL, 45 k/μL, 50 k/μL, 60 k/μL, 70 k/μL, 80 k/μL, 90 k/μL, 100 k/μL, or more, compared to a reference standard (e.g., an untreated subject).

59. The method of embodiment 58, wherein the increase in platelet count comprises maintaining platelet count for at least about 1 week, for at least about 2 weeks, for at least about 3 weeks, for at least about 4 weeks, for at least about 5 weeks, for at least about 6 weeks, for at least about 7 weeks, for at least about 8 weeks, for at least about 9 weeks, or for at least about 10 weeks.

60. The method of any one of embodiments 49 to 59, wherein the subject, e.g., patient, has a platelet count (per liter of blood) of less than about 150 k/μL prior to treatment with iptacopan or a pharmaceutically acceptable salt thereof, e.g., iptacopan hydrochloride.

61. The method of any one of embodiments 49 to 60, wherein the platelet count (per microliter of blood) is normalized after treatment with iptacopan or a pharmaceutically acceptable salt thereof, e.g., iptacopan hydrochloride, to about 150 k/μL or more, about 175 k/μL or more, about 200 k/μL or more, about 225 k/μL or more, about 250 k/μL or more, about 275 k/μL or more, about 300 k/μL or more, about 325 k/μL or more, about 350 k/μL or more, about 375 k/μL or more, about 400 k/μL or more, about 425 k/μL or more, about 450 k/μL or more, e.g., normalized to a range of about 150 k/μL to about 450 k/μL L.

62. The method of any one of embodiments 49 to 61, wherein the method further comprises assessing the level of a biomarker selected from the group consisting of Factor Bb; Wieslab; sC5b-9; and C3/C4 in the subject, e.g., patient.

63. The method of any one of embodiments 49 to 62, wherein the method further comprises assessing the level of a biomarker selected from the group consisting of lactate dehydrogenase (LDH); total bilirubin; reticulocyte count; haptoglobin; anti-platelet antibody level (e.g., directed against GPIIb, GPIIIa, GPIIb/GPIIIa, or GPIbIX); immature platelet fraction; cold agglutinin titer; total antiglobulin titer; and cold agglutinin thermal amplitude.

64. The method of any one of embodiments 49 to 63, wherein the platelet level or level of another biomarker in the subject, e.g., patient, is acquired by sample analysis.

65. A method of treating cold agglutinin disease (CAD) in a subject, e.g., a patient, in need thereof, the method comprising orally administering to the subject, e.g., the patient, iptacopan or a pharmaceutically acceptable salt thereof (e.g., iptacopan hydrochloride) at a dose of about 200 mg, to thereby treat the subject, e.g., patient (wherein the dosing amount refers to the anhydrous free base of iptacopan hydrochloride).

66. The method of embodiment 65, wherein the iptacopan or a pharmaceutically acceptable salt thereof (e.g., iptacopan hydrochloride) is administered to the subject at a dose of about 200 mg twice daily (b.i.d.).

67. The method of embodiment 65 or 66, wherein iptacopan or a pharmaceutically acceptable salt thereof (e.g., iptacopan hydrochloride) is administered for at least 6 weeks, 8 weeks, 10 weeks, 12 weeks, 14 weeks, 16 weeks or longer to the subject, e.g., the patient.

68. The method of any one of embodiments 65 to 67, wherein the therapeutically effective amount of iptacopan or a pharmaceutically acceptable salt thereof (e.g., iptacopan hydrochloride) is administered twice daily (b.i.d.) for at least 12 weeks to the subject, e.g., the patient.

69. The method of any one of embodiments 65 to 68, wherein the method comprises orally administering iptacopan hydrochloride (e.g., iptacopan hydrochloride monohydrate) to the subject, e.g., the patient.

70. The method of any one of embodiments 65 to 69, wherein the method comprises orally administering iptacopan hydrochloride monohydrate (e.g., iptacopan hydrochloride monohydrate Form $H_B$) to the subject, e.g., the patient.

71. The method of any one of embodiments 65 to 70, wherein the subject, e.g., patient, has or is diagnosed with having anemia or hemolysis.

72. The method of any one of embodiments 65 to 71, wherein treating comprises an increase in hemoglobin levels in the subject, e.g., greater than about 0.5 g/dL, 0.75 g/dL, 1.0 g/dL, 1.25 g/dL, 1.5 g/dL, 1.75 g/dL, 2.0 g/dL, 2.5 g/dL, 3.0 g/dL, 4.0 g/dL, 5.0 g/dL, or more, compared to a reference standard (e.g., an untreated subject).

73. The method of any one of embodiments 65 to 72, wherein treating the subject, e.g., patient, comprises increasing the hemoglobin level in the subject, e.g., patient, e.g., by about 0.2 g/dL or more, by about 0.3 g/dL or more, by about 0.4 g/dL or more, by about 0.5 g/dL or more, by about 0.75 g/dL or more, by about 1 g/dL or more, by about 1.25 g/dL or more, by about 1.5 g/dL or more, by about 1.75 g/dL or more, by about 2 g/dL or more, by about 2.25 g/dL or more, about 2.5 g/dL or more, by about 2.75 g/dL or more, or about 3 g/dL or more, e.g., about 2 g/dL or more, e.g., as compared to baseline, e.g., as compared to the hemoglobin level in the subject, e.g., patient, prior to treatment with iptacopan or a pharmaceutically acceptable salt thereof, e.g., iptacopan hydrochloride.

74. The method of any one of embodiments 65 to 73, wherein the method further comprises assessing the level of a biomarker selected from the group consisting of Factor Bb; Wieslab; sC5b-9; and C3/C4 in the subject, e.g., patient.

75. The method of any one of embodiments 65 to 74, wherein the method further comprises assessing the level of a biomarker selected from the group consisting of lactate dehydrogenase (LDH); total bilirubin; reticulocyte count; haptoglobin; anti-platelet antibody level (e.g., directed against GPIIb, GPIIIa, GPIIb/GPIIIa, or GPIbIX); immature platelet fraction; cold agglutinin titer; total antiglobulin titer; and cold agglutinin thermal amplitude.

76. The method of any one of embodiments 65 to 75, wherein the hemoglobin level or level of another biomarker in the subject, e.g., patient, is acquired by sample analysis.

77. Iptacopan or a pharmaceutically acceptable salt thereof, e.g., iptacopan hydrochloride, for use in the treatment of an autoimmune benign hematological disorder, e.g., ITP, CAD, wAIHA or TTP, in a subject, e.g., a patient, in need thereof, wherein the treatment is according to the method of any one of embodiments 1 to 76.

78. A pharmaceutical composition comprising iptacopan or a pharmaceutically acceptable salt thereof, e.g., iptacopan hydrochloride, for use in the treatment of an autoimmune benign hematological disorder, e.g., ITP, CAD, wAIHA, or TTP, in a subject, e.g., a patient, in need thereof, wherein the treatment is according to the method of any one of embodiments 1 to 76.

79. A use of iptacopan or a pharmaceutically acceptable salt thereof, e.g., iptacopan hydrochloride, in the treatment of an autoimmune benign hematological disorder, e.g., ITP, CAD, wAIHA, or TTP, in a subject, e.g., a patient, wherein the treatment is according to the method of any one of embodiments 1 to 76.

80. A use of iptacopan or a pharmaceutically acceptable salt thereof, e.g., iptacopan hydrochloride, in the manufacture of a medicament for the treatment of an autoimmune benign hematological disorder, e.g., ITP, CAD, wAIHA, or TTP, in a subject, e.g., a patient, wherein the treatment is according to the method of any one of embodiments 1 to 76.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof, which may suggest themselves to those skilled in the art without departing from the spirit of the present disclosure and/or scope of the appended claims.

TABLE 1

| List of Abbreviations | |
|---|---|
| ACT | Anatomical Therapeutic Chemical |
| ADCC | Antibody-Dependent Cellular Cytotoxicity |
| AE | Adverse Event |
| ALP | Alkaline Phosphatase |
| ALT | Alanine Aminotransferase |
| ANCOVA | Analysis of Covariance |
| AP | Alternative (complement) Pathway |
| AST | Aspartate Aminotransferase |
| b.i.d. | Bis in die/twice a day |
| BM | Biomarker |
| BMI | Body Mass Index |
| BUN | Blood Urea Nitrogen |
| C1 | Complement Component 1 |
| C3 | Complement Component 3 |
| C3G | C3 Glomerulopathy |
| C4 | Complement Component 4 |
| C5 | Complement Component 5 |
| CAD | Cold Agglutinin Disease |
| CK | Creatinine Kinase |
| ClinRO | Clinician Reported Outcomes |
| CMO&PS | Chief Medical Office and Patient Safety |
| CC | Country Organization |
| COA | Clinical Outcome Assessment |
| CP | Classical (complement) Pathway |
| CRF | Case Report/Record Form (paper or electronic) |
| CRO | Contract Research Organization |
| CSR | Clinical Study Report |
| CTC | Common Terminology Criteria |
| CV | Coefficient of Variation |
| DAT | Direct Antiglobulin Test |

TABLE 1-continued

| List of Abbreviations | |
|---|---|
| DMC | Data Monitoring Committee |
| DQF | Data Query Form |
| ECG | Electrocardiogram |
| EDC | Electronic Data Capture |
| eSAE | Electronic Serious Adverse Event |
| FACIT-Fatigue | Functional Assessment of Chronic Illness Therapy-Fatigue |
| FB | Complement Factor B |
| FDA | Food and Drug Administration |
| FSH | Follicle Stimulating Hormone |
| GCP | Good Clinical Practice |
| GGT | Gamma-Glutamyl Transferase |
| h | Hour |
| HBsAg | Hepatitis B surface Antigen |
| HBV | Hepatitis B Virus |
| HCV | Hepatitis C Virus |
| HIV | Human Immunodeficiency Virus |
| IA | Interim Analysis |
| IB | Investigator's Brochure |
| ICF | Informed Consent Form |
| ICH | International Council for Harmonization of Technical Requirements for Pharmaceuticals for Human Use |
| IEC | Independent Ethics Committee |
| IgAN | IgA Nephropathy |
| IN | Investigator Notification |
| INR | International Normalized Ratio |
| IRB | Institutional Review Board |
| ITP | Immune Thrombocytopenia |
| ITP-PAQ | Immune Thrombocytopenia Purpura Patient Assessment Questionnaire |
| IVIG | Intravenous Immunoglobulins |
| LDH | Lactate Dehydrogenase |
| LFT | Liver Function Test |
| LLN | Lower Limit of Normal |
| LLOQ | Lower Limit of Quantification |
| MedDRA | Medical Dictionary for Regulatory Activities |
| mg | milligram(s) |
| mL | milliliter(s) |
| NCDS | Novartis Clinical Data Standards |
| PD | Pharmacodynamic(s) |
| PK | Pharmacokinetic(s) |
| PNH | Paroxysmal Nocturnal Hemoglobinuria |
| PoC | Proof of Concept |
| PRO | Patient Reported Outcomes |
| PT | Prothrombin Time |
| QMS | Quality Management System |
| QTcF | QT interval corrected by Fridericia's formula |
| RDC | Remote Data Capture |
| SAE | Serious Adverse Event |
| sC5b-9 | soluble Complement Component 5 fraction "b" linked to Complement Component 9 |
| SCR | serum Creatinine |
| SD | Standard Deviation |
| SGOT | Serum Glutamic Oxaloacetic Transaminase |
| SGPT | Serum Glutamic Pyruvic Transaminase |
| SmPC | Summary of Product Characteristics |
| SUSAR | Suspected Unexpected Serious Adverse Reaction |
| TBL | Total Bilirubin |
| TPO-RA | Thrombopoietin Receptor Agonist |
| TTP | Thrombotic Thrombocytopeniaurpura |
| ULN | Upper Limit of Normal |
| wAIHA | Warm Autoimmune Hemolytic Anemia |
| WHO | World Health Organization |
| WoC | Withdrawal of Consent |

TABLE 2

| Glossary of Terms | |
|---|---|
| Additional treatment | Medicinal products that may be used during the clinical trial as described in the protocol, but not as an investigational medicinal product (e.g. any background therapy) |

TABLE 2-continued

| Glossary of Terms | |
|---|---|
| Assessment | A procedure used to generate data required by the study |
| Biologic Samples | A biological specimen including, for example, blood (plasma, serum), saliva, tissue, urine, stool, etc. taken from a study participant |
| Clinical Outcome Assessment (COA) | A measure that describes or reflects how a participant feels, functions, or survives |
| Clinical Trial Team | A group of people responsible for the planning, execution and reporting of all clinical trial activities. Examples of team members include the Study Lead, Medical Monitor, Trial Statistician etc. |
| Coded Data | Personal Data which has been de-identified by the investigative center team by replacing personal identifiers with a code. |
| Cohort | A group of individuals who share a common exposure, experience or characteristic, or a group of individuals followed up or traced over time |
| Control drug | A study drug (active or placebo) used as a comparator to reduce assessment bias, preserve blinding of investigational drug, assess internal study validity, and/or evaluate comparative effects of the investigational drug |
| Cycles | Number and timing or recommended repetitions of therapy are usually expressed as number of days (e.g., q28 days) |
| Discontinuation from study | Point/time when the participant permanently stops receiving the study treatment and further protocol required assessments or follow-up, for any reason. No specific request is made to stop the use of their samples or data. |
| Discontinuation from study treatment | Point/time when the participant permanently stops receiving the study treatment for any reason (prior to the planned completion of study drug administration, if any). Participant agrees to the other protocol required assessments including follow-up. No specific request is made to stop the use of their samples or data. |
| Dosage | Dose of the study treatment given to the participant in a time unit (e.g. 100 mg once a day, 75 mg twice a day) |
| Electronic Data Capture (EDC) | Electronic data capture (EDC) is the electronic acquisition of clinical study data using data collection systems, such as Web-based applications, interactive voice response systems and clinical laboratory interfaces. EDC includes the use of Electronic Case Report Forms (eCRFs) which are used to capture data transcribed from paper source forms used at the point of care |
| End of the clinical trial | The end of the clinical trial is defined as the last visit of the last participant. |
| Enrollment | Point/time of participant entry into the study at which informed consent must be obtained |
| Estimand | A precise description of the treatment effect reflecting the clinical question posed by the trial objective. It summarizes at a population-level what the outcomes would be in the same patients under different treatment conditions being compared. Attributes of an estimand include the population, variable (or endpoint) and treatment of interest, as well as the specification of how the remaining intercurrent events are addressed and a population-level summary for the variable. |
| Healthy volunteer | A person with no known significant health problems who volunteers to be a study participant |
| Intercurrent events | Events occurring after treatment initiation that affect either the interpretation or the existence of the measurements associated with the clinical question of interest. |
| Investigational drug/treatment | The drug whose properties are being tested in the study |
| Medication number | A unique identifier on the label of medication kits |
| Off-site | Describes trial activities that are performed at remote location by an off-site healthcare professional, such as procedures performed at the participant's home. |
| Off-site healthcare Professional (OHP) | A qualified healthcare professional, such as include those used in the study e.g. Nurse, Phlebotomist, Physician, who performs certain protocol procedures for the participant in an off-site location such as a participant's home. |
| Other treatment | Treatment that may be needed/allowed during the conduct of the study (i.e. concomitant or rescue therapy) |
| Part | A sub-division of a study used to evaluate specific objectives or contain different populations. For example, one study could contain a single dose part and a multiple dose part, or a part in participants with established disease and in those with newly-diagnosed disease |
| Participant | A trial participant (can be a healthy volunteer or a patient) |
| Participant number | A unique number assigned to each participant upon signing the informed consent. This number is the definitive, unique identifier for the participant and should be used to identify the participant throughout the study for all data collected, sample labels, etc. |

TABLE 2-continued

| Glossary of Terms | |
|---|---|
| Patient-Reported Outcome (PRO) | A measurement based on a report that comes directly from the patient about the status of a participant's health condition without amendment or interpretation of the patient's report by a clinician or anyone else |
| Period | The subdivisions of the trial design (e.g. Screening, Treatment, Follow-up) which are described in the Protocol. Periods define the study phases and will be used in clinical trial database setup and eventually in analysis |
| Personal data | Participant information collected by the Investigator that is coded and transferred to Novartis for the purpose of the clinical trial. This data includes participant identifier information, study information and biological samples. |
| Premature participant withdrawal | Point/time when the participant exits from the study prior to the planned completion of all study drug administration and/or assessments; at this time all study drug administration is discontinued and no further assessments are planned |
| Re-screening | If a participant fails the initial screening and is considered as a Screen Failure, he/she can be invited once for a new Screening visit after medical judgment and as specified by the protocol |
| Remote | Describes any trial activities performed at a location that is not the investigative site where the investigator will conduct the trial, but is for example a home or another appropriate location |
| Screen Failure | A participant who did not meet one or more criteria that were required for participation in the study |
| Source Data/ Document | Source data refers to the initial record, document, or primary location from where data comes. The data source can be a database, a dataset, a spreadsheet or even hard-coded data, such as paper or eSource |
| Start of the clinical trial | The start of the clinical trial is defined as the signature of the informed consent by the first participant |
| Study treatment | Any drug or combination of drugs or intervention administered to the study participants as part of the required study procedures; includes investigational drug(s), control(s) or background therapy |
| Treatment arm/ group | A treatment arm/group defines the dose and regimen or the combination, and may consist of 1 or more cohorts. |
| Treatment of interest | The treatment of interest and, as appropriate, the alternative treatment to which comparison will be made. These might be individual interventions, combinations of interventions administered concurrently, e.g. as add-on to standard of care, or might consist of an overall regimen involving a complex sequence of interventions. This is the treatment of interest used in describing the related clinical question of interest, which might or might not be the same as the study treatment. |
| Unique Prior Therapy | Any pharmaceutical agent or type of non-pharmacological intervention (e.g., splenectomy, plasmapheresis) administered with the intention to treat the indications under study. Transfusions of blood products are not accounted as prior therapies. Any unique prior therapy will be counted once, even if it is stopped and restarted or given in different combinations. Different corticosteroids will be counted as a single unique prior therapy, whereas different members of other drug classes such as thrombopoietin receptor agonists will be counted as different unique prior therapies. |
| Variable (or endpoint) | The variable (or endpoint) to be obtained for each participant that is required to address the clinical question. The specification of the variable might include whether the participant experiences an intercurrent event. |
| Withdrawal of study consent (WoC)/ Opposition to use of data/biological samples | Withdrawal of consent from the study occurs when the participant explicitly requests to stop use of their data and biological samples (opposition to use data and biological samples) AND no longer wishes to receive study treatment, AND does not agree to further protocol required assessments. This request should be in writing (depending on local regulations) and recorded in the source documentation.<br>Opposition to use data/biological samples occurs in the countries where collection and processing of personal data is justified by a different legal reason than consent. |

Example 1. An Adaptive Basket Study to Evaluate Efficacy and Safety of LNP023 (Iptacopan) Hydrochloride, Administered Oral, Twice Daily in Adult Patients with Autoimmune Benign Hematological Disorders (ITP or CAD)

Purpose

This trial is a proof-of-concept study to assess the potential for iptacopan treatment in different autoimmune benign hematological disorders with evidence of complement activation in at least a subset of patients. The study is an adaptive basket study (FIG. 1) with two initial cohorts/indications, namely ITP and CAD. Additional cohorts/indications, such as wAIHA and/or TTP may be added by protocol amendment. The study will assess the effects of study treatment iptacopan on a range of efficacy assessments relevant to autoimmune benign hematological disorders, specifically ITP and CAD, depending on the cohort. For Cohort 1 (ITP), a key endpoint is the ability of iptacopan to induce an increase in the platelet count in a subject, e.g., a platelet count increase to ≥50 k/μL compared to baseline sustained for at least 2 consecutive weeks. For Cohort 2 (CAD), a key endpoint is the ability of iptacopan to induce an increase in hemoglobin levels, e.g., a hemoglobin level increase of ≥1.5 g/dL compared to baseline sustained for at least 2 consecutive weeks.

This study will serve as the pivotal trial for the development of iptacopan as a treatment for patients with an autoimmune benign hematological disorder, such as ITP or CAD. Data from the 12-week core treatment period (Day 85) of this study will provide the pivotal efficacy and safety data. The 24-month Extension Treatment phase will provide further long-term safety and efficacy data on iptacopan in patients with an autoimmune benign hematological disorder, such as ITP or CAD.

Investigational Study Drug

The form of the investigational study drug, iptacopan hydrochloride, chosen for this Phase 3 study is a monohydrate Form $H_B$ as shown in the formula below:

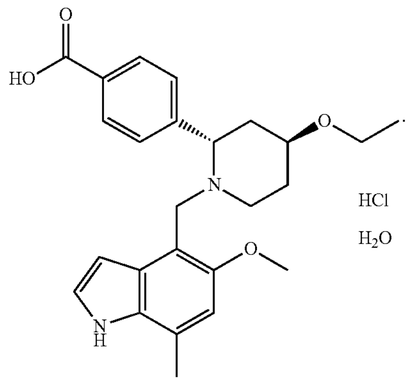 [SMILES: CCO[C@H]1CCN(Cc2c(OC)cc(C)c3[nH]ccc23)[C@H](c2ccc(C(=O)O)cc2)C1 ; Cl ; O]

(2S,4S)-2-(4-Carboxyphenyl)-4-ethoxy-1-[(5-methoxy-7-methyl-1H-indol-4-yl)methyl]piperidin-1-ium chloride-water (1/1)

Accordingly, in Example 1, "iptacopan" means iptacopan hydrochloride monohydrate Form $H_B$. Iptacopan hydrochloride monohydrate Form $H_B$ and methods for its preparation are disclosed in U.S. Ser. No. 63/026,637 and U.S. Ser. No. 63/052,699, published as WO 2021/234544, each of which is incorporated herein by reference in its entirety.

Primary Objectives and Endpoints

The primary objective depends on the subject cohort. For Cohort 1 (ITP), the primary objective is to assess the ability of iptacopan to induce an increase (e.g., clinically meaningful increase) in platelet count in participants without the use of a rescue therapy. The endpoint is observation of a platelet count increase to ≥50 k/μL sustained for at least 2 consecutive weeks during Phase A of the treatment period (12 weeks). For Cohort 2 (CAD), the primary objective is to assess the ability of iptacopan to induce an increase (e.g., clinically meaningful increase) in hemoglobin levels in participants without the use of a rescue therapy. The endpoint is observation of a hemoglobin level increase of ≥1.5 g/dL sustained for at least 2 consecutive weeks during Phase A of the treatment period (12 weeks).

Secondary Objectives and Endpoints/Estimands

The secondary objectives are to:

To assess the time to first response. For Cohort 1 (ITP), the time to first platelet count of ≥50 k/μL will be assessed. For Cohort 2 (CAD), the time to first hemoglobin level of ≥1.5 g/dL above baseline will be assessed.

To assess the duration of response during Part A of the treatment period (12 weeks). For Cohort 1 (ITP), the duration during which platelet count remains ≥50 k/μL will be measured. For Cohort 2 (CAD), the duration during which hemoglobin level remains ≥1.5 g/dL above baseline will be measured.

To assess the magnitude of response during Part A of the treatment period (12 weeks). For Cohort 1 (ITP), the magnitude of platelet count increase from baseline will be measured. For Cohort 2 (CAD), the magnitude of hemoglobin level increase from baseline will be measured.

To assess the need for rescue therapy during Part A of the treatment period (12 weeks). The endpoint for both Cohorts 1 and 2 will be whether or not rescue therapy was utilized during the treatment period.

To assess the safety and tolerability of iptacopan in a subject with an autoimmune benign hematological disorder, particularly ITP and CAD, during Part A of the treatment period (12 weeks). For both Cohorts 1 and 2, subject safety parameters will be closely monitored and evaluations performed, such as checking vital signs, adverse events, hematology, blood chemistry, reproductive and thyroid hormones, coagulation, urinalysis, and ECG.

To assess the pharmacokinetics of iptacopan during Part A of the treatment period (12 weeks). For both Cohorts 1 and 2, iptacopan PK parameters including Cmax, AUCtau, AUClast, Ctrough, and Tmax levels in the subjects will be evaluated.

To assess the effect of iptacopan on relevant disease biomarks during Part A of the treatment period (12 weeks). For Cohort 2 (CAD) only, levels of lactate dehydrogenase (LDH), total bilirubin, reticulocyte count, and haptoglobin levels will be assessed.

Additional objectives include:

To assess the effect of iptacopan on complement pathway biomarkers. For both Cohorts 1 and 2, levels of biomarkers including Factor Bb, Wieslab, sC5b-9 and C3/C4 will be assessed.

To assess the effect of iptacopan on additional disease biomarkers. For Cohort 1 (ITP), levels of anti-platelet antibodies and immature platelet fraction will be measured. For Cohort 2 (CAD), direct antiglobulin levels (DAT), cold agglutinin titer, and cold agglutinin thermal amplitude will be measured.

To assess the effect of iptacopan on quality of life. For both Cohorts 1 and 2, the patient-reported overall fatigue severity and health-related quality of life, where the endpoint is determined by the change from baseline in patient-reported outcomes score for FACIT-Fatigue, Patient Global Impression of Severity (PGIS), EuroQol 5-level EQ-5D version (EQ-5D-5L) and Short-form 36 health survey questionnaire version 2 (SF-36 v2) at Week 26 will be assessed. For Cohort 1 (ITP) only, the ITP patient assessment questionnaire (ITP-PAQ) will additionally be administered.

To assess the effect of iptacopan withdrawal on disease biomarker levels. For Cohort 1 (ITP), the platelet count will be monitored. For Cohort 2 (CAD), biomarkers including hemoglobin, LDH, total bilirubin, reticulocyte, and haptoglobulin levels will be assessed.

To assess the impact of iptacopan administration on bleeding in the subject. For Cohort 1 (ITO) only, the WHO bleeding score will be assessed.

To assess the effect of long-term treatment with iptacopan on disease biomarkers in responders during Part B of the treatment period (24 months). For both Cohorts 1 and 2, changes in hematological parameters including platelet count and hemoglobin levels will be assessed, along with disease-specific biomarkers. For Cohort 1 (ITP), disease specific biomarkers include levels of anti-platelet antibodies and immature platelet fraction. For Cohort 2 (CAD), disease specific biomarkers include direct antiglobulin levels (DAT), cold agglutinin titer, and cold agglutinin thermal amplitude.

To assess the ability to taper or discontinue any concomitant background therapy in responders during Part B of the treatment period (24 months). For both Cohorts 1 and 2, the ability to taper or discontinue any concomitant background therapy for the cohorts and subjects where this is applicable will be assessed.

To perform genetic research to better understand the safety and efficacy of iptacopan (including adverse events/serious adverse events, safety laboratory parameters and vital signs)

The primary estimand is an understanding of the effect of iptacopan on (type of response) in participants with autoimmune benign hematological disorders, regardless of study treatment discontinuation or start of new therapy. There are no secondary estimands associated with this study.

Study Design Rationale

This Phase 2 study is designed as an exploratory, multicenter, single-arm (within each cohort), open label trial, non-confirmatory adaptive basket study to investigate the efficacy, safety, and pharmacokinetics of oral, twice daily iptacopan in patients with an autoimmune benign hematological disorder (ITP or CAD). A single arm design (within each cohort) has been chosen for this study for the following reasons:

A placebo-controlled design is deemed unethical because autoimmune benign hematological disorders including ITP and CAD are severe, ultra-rare, rapidly progressing disease requiring early treatment. Moreover, in countries where SoC is available, a placebo arm will not be justified.

The single arm, open-label design is widely used in rare diseases due to challenges associated with conducting studies in these patient populations (Bell S A, et al. (2014) A comparison of interventional clinical trials in rare versus non-rare diseases: an analysis of ClinicalTrials.gov. Orphanet J Rare Dis; 9:170) as a randomized controlled study (vs. SoC) would require a large sample size. Due to the rare nature of the disease and the challenge recruiting this patient population in a reasonable timeframe, a single arm trial design will allow earlier availability of data for a potentially beneficial treatment for patients with autoimmune benign hematological disorders including ITP and CAD.

Several measures have been included in the study design to minimize biases associated with this single arm open-label design including primary and majority of secondary and efficacy endpoints that will be objectively measured via laboratory assessments (i.e. platelets, hemoglobin and others).

A multicenter setting is chosen for the study to ensure adequate recruitment and representative enrollment of patients from a wide range of geographic regions for this rare indication.

Secondary efficacy endpoints include key hematological parameters that are clinically important to patient prognosis, including changes in disease-specific biomarkers and improvements in hematological parameters (platelet count and hemoglobin).

Study Design

This Phase 2 study is a multicenter, single arm, open-label trial in adult patients diagnosed with an autoimmune benign hematological disorder, specifically ITP and CAD, and who further are diagnosed with thrombocytopenia (in the case of ITP) or anemia and hemolysis (in the case of CAD). The study will consist of four periods as showing in FIG. 1.

A screening period lasting up to 5 weeks

A 12-week dual cohort, open-label core treatment period for the primary efficacy and safety analysis (Part A)

Follow up/washout period

A 24 month open-label Extension Treatment period to assess long-term safety, tolerability and efficacy of iptacopan (Part B)

The total study duration from screening until end of study visit (EOS) is approximately 5 months for subjects not meeting the primary endpoint (non-responders). After initial treatment in Part A, subjects meeting the primary endpoint (responders) will be offered to join Part B after a washout. In Part B, subjects responding to treatment will be provided long-term access to iptacopan (24 months of treatment). The total study duration for responders is up to 30 months (FIG. 1). Safety and efficacy assessments will be conducted at visits as specified in the Assessment Schedule (FIGS. 2-3). Pharmacokinetic (PK) and biomarker (BM) samples will also be collected.

A screening period ensures differential diagnosis of either ITP or CAD and also ensures that all participants meet the inclusion criteria, such vaccination status. The screening period may be up to 5 weeks to assess eligibility. Following the screening period, the subjects begin Part A of the treatment period. Part A includes a treatment period of 12 weeks (Day 1 to Day 85), which comprises twice daily (b.i.d.) administration of 200 mg iptacopan or a pharmaceutically acceptable salt thereof. Any pre-existing background therapy (if relevant) will remain unchanged during Part A. Subjects will have weekly assessments for the first 4 weeks of Phase A, followed by assessments every 2 weeks for the latter 8 weeks. Safety and efficacy assessments will be conducted and biomarker (BM) samples collected at visits as specified in the Assessment Schedule for Part A (FIG. 2). There will also be two PK profiling days in Part A. The Part A treatment duration of 12 weeks is considered appropriate to assess the effect of iptacopan on the primary and secondary efficacy endpoints as well as safety and tolerability.

At the end of Part A, subjects will be classified as responders or as non-responders based on whether or not they meet the cohort-specific primary endpoint (e.g., platelet count or hemoglobin levels). Non-responders (and responders not wanting to move on to Part B) will have a safety follow-up period of 4 weeks after the last administration or iptacopan. Participants will undergo study completion evaluations and will complete the study during EOS visit approximately 4 weeks after the last administration of iptacopan. All participants will have a follow-up call approximately 30 days after the last visit.

Responders will be offered to join the optional treatment extension in Part B. Prior to the start of Part B, all eligible subjects will undergo a washout period lasting up to 4 weeks. After the washout period the patients will have EOS Part A/Day 1 Part B visit. Participants reaching a critical safety cut-off level at any follow-up/washout visit will have the opportunity to shorten the washout and move to EOS Part A/Day 1 Part B visit before completion of the 4 weeks of wash-out.

Following Part A and the subsequent washout period, eligible responders will continue to the Part B treatment period. Phase B period will last up to 24 months and will provide long-term safety data and efficacy data on iptacopan in autoimmune benign hematological disorders, particularly ITP and CAD. Part B includes twice daily (b.i.d.) administration of 200 mg iptacopan or a pharmaceutically acceptable salt thereof. Any pre-existing background therapy may be tapered off after 2 weeks of treatment. Assessments during Part B are summarized herein and in FIG. 3. After completion of the treatment phase, the subjects will move to a 4 week follow up period and complete the study at EOS for Part B. All subjects will have a follow up assessment approximately 30 days after the last treatment.

An interim analysis (IA) will be performed for each cohort separately. The first IA will be performed at the time when approximately half the adult participants have completed 12 weeks of study treatment. The intent of this IA is to provide preliminary evidence of efficacy and safety of iptacopan. A second IA will be performed after all participants within a cohort complete Part A of the treatment period (12 weeks). Additional IAs may be conducted to support decision making concerning the current clinical study, or in the case of any safety concerns. The IA will include analyses of the primary endpoint (complete TMA response) at 12 weeks and its components [hematological normalization (platelet count and hemoglobin levels) and monitoring of other disease-specific biomarkers] relevant to clinical benefit in patients with an autoimmine benign hematological disorder. In addition, safety endpoints (including vital signs, safety labs, adverse events, serious adverse events, discontinuations, etc.) will be reviewed.

A volume smaller than a typical blood donation is planned to be collected over a period of 5 months (Part A) or 25 months (Part B), from each participant as part of the study. The approximate volumes will be determined. Timings of blood sample collection are outlined in the Assessment Schedule (FIGS. 2-3). A summary blood log is provided in the laboratory manual. Instructions for sample collection, processing, storage and shipment are also available in the laboratory manual.

The study population will include a total of about 30 enrolled participants across two cohorts. For Cohort 1 (ITP), approximately 20 participants with primary ITP will be enrolled; approximately 10 participants each with high and low complement activity, respectively. For Cohort 2 (CAD), approximately 10 participants with primary CAD will be enrolled. A Patient Selection Committee may be established to review patient's eligibility and confirm patient's enrollment into the study. As the study will run in multiple centers worldwide where clinical practice may differ, the Committee may ensure an independent review of the patient selection criteria to standardize any geographical differences which may exist in diagnosing primary ITP or CAD.

Dose and Duration Rationale

Iptacopan at 200 mg b.i.d. (wherein the dosing amount refers to the anhydrous free base of iptacopan) has been selected for this study based on the totality of safety, efficacy and favorable benefit-risk ratio data from the first other studies, including first in human (FIH) studies and the Phase 2 studies in C3 Glomerulopathy (C3G) (CLNP023X2202 and CLNP023B12001B), paroxysmal nocturnal hemoglobinuria (PNH) (CLNP023X2204 and CLNP023X2201) and IgA nephropathy (IgAN) (CLNP023X2203).

In the FIH studies, there was rapid suppression of the AP activity (Wieslab) with approximately 80% or greater inhibition achieved at two hours post-dose for participants receiving single dose of 200 mg iptacopan. The suppression of the AP (80% or greater inhibition) was sustained over 14 days of dosing at 200 mg b.i.d. The exposure-response model developed with data from the FIH study with iptacopan in healthy volunteers predicts that a dose of about 200 mg b.i.d. would be needed to achieve >90% inhibition of the AP (Wieslab assay) in most participants. Preclinical studies supported acceptable safety margins for human exposure following 200 mg b.i.d. dosing.

Given the observed PK/PD profile in a first in human study in healthy volunteers, a 200 mg b.i.d dose of iptacopan is selected for this study.

Screening

The screening assessments will be followed as outlined herein, e.g., in FIG. 1. Prior to initiation of the study, the subjects will participate in a screening period, in which participants who have not received the required vaccinations should be vaccinated. Vaccines should cover as many serotypes as possible (including meningococcal serotypes A, C, Y, W-135 and B). To minimize patient burden, the use of multivalent vaccines is recommended as locally available and per local guidelines and regulations (e.g. quadrivalent vaccine for *N. meningitidis*, which covers serotypes A, C, Y and W-135 and Pneumovax-23 which covers 23 *S. pneumoniae* serotypes). For the vaccination type and booster requirements use local guidelines, and locally available vaccines (and refer to the package insert). Vaccinations should be started as early as possible. Patients who have not been vaccinated prior to initiating iptacopan study treatment should receive appropriate prophylactic antibiotics prior to and for at least 2 weeks after vaccination. If eligibility criteria are not met, the study participant should be considered as having failed screening and should not proceed further. The study participant can be re-screened.

Treatment Period A

Participants who are confirmed to meet the eligibility criteria will proceed to the open-label core treatment period. Treatment with iptacopan at a dose of 200 mg b.i.d. will start on the first day (Day 1) and continue for 12 weeks with study visits and corresponding assessments according to the schedule described in FIG. 2.

Because of the known increased risk of infections with encapsulated bacteria, all participants will be provided with a Patient Safety Card. Participants will be instructed to be vigilant for any clinical sign of bacterial infections and to contact the investigator or local physician immediately in case of suspicion of infection. If indicated, antibiotic treatment should be started as soon as possible.

Participants who discontinue iptacopan study treatment administration during the core treatment period should not discontinue from the study (unless consent is withdrawn), but complete all visits and assessments up to Week 12 visit of the core treatment period. For these patients, the Week 12 visit assessments and the 7 days-post-EoT safety follow up phone call should be performed as End of Study (EoS) visit/assessments for the trial as they will not pursue in the Extension Treatment phase of the study.

The core treatment period will end with the completion of the Week 12 visit assessments. In the event that a study participant withdraws consent at any time during the core treatment period, a last visit shall be performed to record patient's withdrawal visit assessments should be performed as End of Study (EoS) visit for the trial).

Treatment Period B

After completion of the 26 weeks treatment period A, study participants be provided with a washout period of approximately 4 weeks before being categorized as non-responders or responders. All responders will continue study treatment with iptacopan and enter the Treatment Period B, or the Extension Treatment Period, which will run for up to 24 months. The study visits and assessments detailed in FIG. 3 will be followed.

Treatment Assignment

No randomization will be performed in this study; all eligible participants will receive open-label iptacopan 200 mg b.i.d. treatment.

Study Population

The study will enroll patients ≥18 years of age, diagnosed with either ITP or CAD. For Cohort 1 (ITP), approximately 20 participants with primary ITP will be enrolled wherein about 10 participants exhibit high complementation activation and the other 10 participants exhibit low complement activation, respectively. For Cohort 2 (CAD), approximately 10 participants with primary CAD will be enrolled.

Inclusion Criteria

Participants eligible for inclusion in this study must meet all of the following criteria:

1. Written informed consent
2. Vaccination against *Neisseria meningitidis* and *Streptococcus pneumoniae* infections is required and vaccination against *Haemophilus influenzae* infection is recommended prior to the start of treatment.

Cohort 1(ITP) Specific Inclusion Criteria

3. Male and female participants aged ≥18 years at baseline with a diagnosis of primary ITP
4. Participants should have received at least 1 unique prior therapy, defined as any pharmaceutical agent or type of non-pharmacological intervention (e.g., splenectomy) administered with the intention to treat ITP
5. Sustained thrombocytopenia Cohort 2 (CAD) Specific Inclusion Criteria 6. Male and female participants aged ≥18 years at baseline with a diagnosis of primary CAD, including CAD arising in the setting of a low-grade lymphoproliferative disorder a) not requiring any therapy and b) without evidence of splenomegaly, hepatomegaly, or diffuse lymphadenopathy
7. Positive direct antiglobulin test for C3d only and cold agglutinin titer of 264 at 4° C.
8. Laboratory evidence of ongoing hemolysis
9. Sustained anemia
10. Participants should have received at least 1 unique prior therapy, defined as any pharmaceutical agent or type of non-pharmacological intervention (e.g., plasmapheresis) administered with the intention to treat CAD Exclusion Criteria Participants meeting any of the following criteria are not eligible for inclusion in this study:

All Cohorts

- Use of other investigational drugs at the time of enrollment, or within 5 half-lives of enrollment, or within 30 days, whichever is longer; or longer if required by local regulations
- Past or concomitant use of medications prohibited by the protocol
- Known or suspected hereditary or acquired complement deficiency
- History of primary or secondary immunodeficiency, including a positive HIV test result
- Chronic infection with Hepatitis B or C virus
- History of recurrent invasive infections caused by encapsulated organisms, including *N. meningitidis, S. pneumoniae*, or *H. influenzae*
- Presence or suspicion (based on judgment of the investigator) of any active infection within 14 days prior to first study drug administration.
- Any medical condition deemed likely to interfere with the participant's participation in the study
- Any malignant disease diagnosed within the past 5 years, with the exception of localized non-melanoma skin cancer, in situ cervical cancer, or, for CAD, a low-grade lymphoproliferative disorder.
- History of bone marrow/hematopoietic stem cell or solid organ transplantation.
- Women of child-bearing potential, defined as all women physiologically capable of becoming pregnant, unless they are using effective methods of contraception during dosing of investigational drug and for 1 week after last iptacopan dose Cohort 1 (ITP) Specific Exclusion Criteria

- Secondary ITP, as may arise in the setting of certain autoimmune disorders, immunodeficiency syndromes, infections, malignancies, and drug treatments
- No ITP-directed background therapy permitted, with the exception of a thrombopoietin receptor agonist (TPO-RA) or low-dose corticosteroid, as long as stable dosage for at least 4 weeks prior to baseline
- Abnormal coagulation screening labs (PT/INR, PTT)

Cohort 2 (CAD) Specific Exclusion Criteria

- Secondary cold agglutinin syndrome, as may arise in the setting of certain infections, autoimmune disorders, and malignancies (with the exception of a low-grade lymphoproliferative disorder)
- No CAD-directed background therapy permitted In case of use of oral contraception, women should have been stable on the same pill for a minimum of 3 months before taking investigational drug. Women are considered post-menopausal if they have had 12 months of natural (spontaneous) amenorrhea with an appropriate clinical profile (e.g. age appropriate, history of vasomotor symptoms). Women are considered not of childbearing potential if they are post-menopausal or have had surgical bilateral oophorectomy (with or without hysterectomy), total hysterectomy or bilateral tubal ligation at least six weeks ago. In the case of oophorectomy alone, only when the reproductive status of the woman has been confirmed by follow up hormone level assessment is she considered not of child bearing potential. If local regulations deviate from the contraception methods listed above to prevent pregnancy, local regulations apply and will be described in the ICF.

Treatment

All participants starting study treatment in this single arm open label study will receive iptacopan 200 mg b.i.d. No other treatment beyond iptacopan is included in this trial (see Table 3 for details of investigational drug).

TABLE 3

| Investigational Drug | | | | |
|---|---|---|---|---|
| Investigational/ Control Drug | Pharmaceutical Dosage Form | Route of Administration | Presentation | Sponsor (global or local) |
| Iptacopan, 200 mg | Hard gelatin capsule | Oral use | Open label, patient specific kits | Sponsor (global) |

Treatment Duration

The planned duration of core treatment period is 12 weeks (Part A) followed by an Extension Treatment period of up to 24 months (Part B). Participants may be discontinued from study treatment earlier due to unacceptable toxicity and/or study treatment is discontinued at the discretion of the investigator or the participant.

If a participant discontinues study treatment for any reason during the core treatment period, every effort must be made to continue with the study assessments up to Week 12.

Prohibited Medication

Use of the treatments and procedures listed below in Table 4 are not allowed during iptacopan administration:

TABLE 4

| List of Prohibited Medications | | |
|---|---|---|
| Medication | Prohibition period | Action taken |
| Complement inhibitor therapy other than iptacopan | Any time prior to enrollment until EOS | Discontinue study treatment |
| Targeted B-lymphocyte depleting therapy (incl. rituximab) | 3 months prior to baseline until EOS | Discontinue study treatment |
| Systemic corticosteroids | 2 weeks prior to baseline until EOS. Exceptions: Low-dose corticosteroid (prednisone-equivalent of ≤10 mg daily) allowed for ITP participants only as long as stable dosage for at least 4 weeks prior to baseline, rescue therapy or one-time prophylaxis for hypersensitivity reactions. | Discontinue study treatment, unless covered by exceptions. |
| Other immunosuppressive or antineoplastic agents, including but not limited to anti-Rho(D) IG, bendamustine, bortezomib, cyclosporine, cyclophosphamide, IVIG, mycophenolate mofetil, vincristine | 1 month prior to baseline until EOS. Exception (on study): Rescue therapy. | Discontinue study treatment, unless covered by exception |
| Other regimens to treat the primary indication | 2 weeks prior to baseline until EOS. Exceptions: Thrombopoeitin receptor agonists (TPO-RAs) (single agent allowed for ITP participants only as long as stable dosage for at least 4 weeks prior to baseline). | Discontinue study treatment, unless covered by exceptions |
| Anti-thrombotic or anti-platelet therapy | Prohibited for ITP Cohort 1 only: 2 weeks prior to baseline until EOS. | Discontinue study treatment, unless covered by exception |
| Live vaccines | Prohibited for the entire study treatment duration | |
| Gemfibrozil | Gemfibrocil must be interrupted at least 48 hours before first iptacopan dose until end of iptacopan treatment (and replaced with another appropriate medication used for that indication) | |
| Strong inhibitors of CYP2C8 such as clopidogrel | Strong inhibitors of CYP2C8 must be interrupted 7 days before first iptacopan dose until end of iptacopan treatment (and replaced with another appropriate medication used for that indication) | |

TABLE 4-continued

| List of Prohibited Medications | | |
|---|---|---|
| Medication | Prohibition period | Action taken |
| "Sensitive substrates" for the efflux transporter P-gp or P-gp substrates with narrow therapeutic index (NTI) (e.g., digoxin, quinidine, paclitaxel, fentanyl, phenytoin) | Medication to be interrupted 48 hours before first iptacopan dose | |

Visit Schedule and Assessments

The assessment schedules shown in FIGS. 2-3 list which assessments as well as when they are performed. Participants who discontinue from iptacopan study treatment for any reason during the core treatment period should continue in the study up to Week 12 visit, completing all scheduled visits assessments. Participants who discontinue from iptacopan study treatment during the Extension Treatment period of the study for any reason should continue in the study up to the 24 month visit completing all scheduled visit assessments.

In both FIGS. 2 and 3, the "X" in the tables denotes the assessments to be recorded in the clinical database or received electronically from a vendor. The "S" in the table denotes the assessments that are only in the participant's source documentation and do not need to be recorded in the clinical database.

When the following assessments are scheduled to be performed at the same time point, the following sequence is proposed:

1. PROs/ClinROs
2. ECGs
3. Vital signs
4. Blood sample collections
5. Drug administration For PK profiling days, every effort should be made to take the PK sample at the protocol-specified time. Other assessments, e.g., PROs, ECGs and vital signs, can be taken after the PK sample.

Efficacy

Efficacy/pharmacodynamic assessments will be collected at the time points defined in the Assessment schedules shown in FIGS. 2-3 for subjects in each of Cohort 1 and Cohort 2.

Safety

Safety assessments are provided below in Table 5, to be carried out in conjunction with the assessment schedules in FIGS. 2-3.

TABLE 5

| List of safety assessments | |
|---|---|
| Assessment | Specification |
| Physical examination | A complete physical examination will include the examination of general appearance, skin, neck (including thyroid), eyes, ears, nose, throat, lungs, heart, abdomen, back, lymph nodes, extremities, vascular, and neurological. If indicated based on medical history and/or symptoms, rectal, external genitalia, breast, and pelvic exams will be performed. A short physical exam will include the examination of general appearance. A short physical exam will be at all visits starting from Day 1 except where a complete physical examination is required (see above). Information for all physical examinations must be included in the source documentation at the study site. Clinically relevant findings that are present prior to signing informed consent must be recorded on the appropriate CRF that captures medical history. Significant findings made after signing informed consent which meet the definition of an Adverse Event must be recorded as an adverse event. |
| Vital signs | Vital signs will include the collection of body temperature (recorded in ° C.), blood pressure (BP) and pulse measurements. The same route (temporal, tympanic, or axillary) and modality (temporal scanner, tympanic probe, thermometer) for body temperature monitoring should be used for ongoing participants to allow for accurate evaluation of the temperature trend. After the participant has been sitting for 3 minutes, with back supported and both feet placed on the floor, systolic and diastolic BP will be measured using an automated validated device, e.g., OMRON with an appropriately sized cuff. In case the cuff sizes available are not large enough for the participant's arm circumference, a sphygmomanometer with an appropriately sized cuff may be used. If vital signs are out-of-range two additional readings can be obtained, so that up to three consecutive assessments are made, with the participant seated quietly for approximately five minutes preceding each repeat assessment. In case of repeated vital assessments, the eCRF should contain the last results. |
| Height and weight | Height in centimeters (cm) and body weight (to the nearest 0.1 kilogram (kg) in indoor clothing, but without shoes) will be measured. Body mass index (BMI) will be calculated using the following formula: BMI = Body weight (kg)/[Height (m)]$^2$ |

An adverse event (AE) is any untoward medical occurrence (e.g. any unfavorable and unintended sign [including abnormal laboratory findings], symptom or disease) in a clinical investigation participant after providing written informed consent for participation in the study. Therefore, an AE may or may not be temporally or causally associated with the use of a medicinal (investigational) product. The occurrence of adverse events must be sought by non-directive questioning of the participant at each visit during the study (see, e.g., FIGS. 2-3). Adverse events also may be detected when they are volunteered by the participant during or between visits or through physical examination findings, laboratory test findings, or other assessments.

Adverse events must be recorded under the signs, symptoms, or diagnosis associated with them, accompanied by the following information (as far as possible):

1. The severity grade:
   - mild: usually transient in nature and generally not interfering with normal activities
   - moderate: sufficiently discomforting to interfere with normal activities
   - severe: prevents normal activities
2. Its relationship to the study treatment. If the event is due to lack of efficacy or progression of underlying illness (i.e. progression of the study indication) the assessment of causality will usually be 'Not suspected.' The rationale for this guidance is that the symptoms of a lack of efficacy or progression of underlying illness are not caused by the trial drug, they happen in spite of its administration and/or both lack of efficacy and progression of underlying disease can only be evaluated meaningfully by an analysis of cohorts, not on a single participant
3. Its duration (start and end dates or ongoing) and the outcome must be reported
4. Whether seriousness criteria have been met
5. Action taken regarding with study treatment.

All adverse events must be treated appropriately. Treatment may include one or more of the following:

Dose not changed

Dose Reduced/increased

Drug interrupted/permanently discontinued

6. Its outcome

Conditions that were already present at the time of informed consent should be recorded in medical history of the participant. Adverse events (including lab abnormalities that constitute AEs) should be described using a diagnosis whenever possible, rather than individual underlying signs and symptoms.

Adverse event monitoring should be continued for at least 30 days following the last dose of study treatment.

Once an adverse event is detected, it must be followed until its resolution or until it is judged to be permanent (e.g. continuing at the end of the study), and assessment must be made at each visit (or more frequently, if necessary) of any changes in severity, the suspected relationship to the interventions required to treat it, and the outcome.

Abnormal laboratory values or test results constitute adverse events only if they fulfill at least one of the following criteria:

they induce clinical signs or symptoms they are considered clinically significant they require therapy Clinically significant abnormal laboratory values or test results must be identified through a review of values outside of normal ranges/clinically notable ranges, significant changes from baseline or the previous visit, or values which are considered to be non-typical in participant with the underlying disease.

An serious adverse event (SAE) is defined as any adverse event [appearance of (or worsening of any pre-existing)] undesirable sign(s), symptom(s), or medical conditions(s) which meets any one of the following criteria:

- fatal
- life-threatening: life-threatening in the context of a SAE refers to a reaction in which the participant was at risk of death at the time of the reaction; it does not refer to a reaction that hypothetically might have caused death if it were more severe (please refer to the ICH-E2D Guidelines).
- results in persistent or significant disability/incapacity
- constitutes a congenital anomaly/birth defect
- requires inpatient hospitalization or prolongation of existing hospitalization, unless hospitalization is for:
  - routine treatment or monitoring of the studied indication, not associated with any deterioration in condition
  - elective or pre-planned treatment for a pre-existing condition that is unrelated to the indication under study and has not worsened since signing the informed consent
  - social reasons and respite care in the absence of any deterioration in the participant's general condition
  - treatment on an emergency outpatient basis for an event not fulfilling any of the definitions of a SAE given above and not resulting in hospital admission
- is medically significant, e.g. defined as an event that jeopardizes the participant or may require medical or surgical intervention to prevent one of the outcomes listed above Medical and scientific judgment should be exercised in deciding whether other situations should be considered serious reactions, such as important medical events that might not be immediately life threatening or result in death or hospitalization but might jeopardize the participant or might require intervention to prevent one of the other outcomes listed above. Such events should be considered as "medically significant." Examples of such events are intensive treatment in an emergency room or at home for allergic bronchospasm, blood dyscrasias, or convulsions that do not result in hospitalization or development of dependency or abuse (please refer to the ICH-E2D Guidelines).

All new malignant neoplasms will be assessed as serious under "medically significant" if other seriousness criteria are not met. Any suspected transmission via a medicinal product of an infectious agent is also considered a serious adverse reaction. All reports of intentional misuse and abuse of the product are also considered serious adverse event irrespective if a clinical event has occurred.

Study Discontinuation and Completion

Discontinuation of study treatment for a participant occurs when study treatment is permanently stopped for any reason (prior to the planned completion of study treatment administration, if any) and can be initiated by either the participant or the investigator.

Study completion is defined as when the last participant finishes their End of Study visit and any repeat assessments associated with this visit have been documented and followed-up appropriately by the Investigator or, in the event of an early study termination decision, the date of that decision. Participants who complete the study may be eligible to enroll in a single-arm open-label iptacopan rollover extension program (REP). Participants who prematurely withdraw from the study for any reason are not eligible to enroll in the REP.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method of treating cold agglutinin disease (CAD) in a subject, in need thereof, the method comprising administering to the subject a therapeutically effective amount of iptacopan or a pharmaceutically acceptable salt thereof to thereby treat the subject.

2. The method of claim 1, wherein the therapeutically effective amount of iptacopan or a pharmaceutically acceptable salt thereof comprises a dose of about 50 mg to about 200 mg, wherein the dosing amount refers to the anhydrous free base of iptacopan hydrochloride.

3. The method of claim 1, wherein the therapeutically effective amount of iptacopan or a pharmaceutically acceptable salt thereof is administered twice daily (b.i.d.) to the subject.

4. The method of claim 1, wherein the method comprises orally administering iptacopan or a pharmaceutically acceptable salt thereof to the subject.

5. The method of claim 1, wherein the method comprises orally administering iptacopan or a pharmaceutically acceptable salt thereof, at a dose of about 200 mg twice daily (b.i.d.) to the subject, wherein the dosing amount refers to the anhydrous free base of iptacopan hydrochloride.

6. The method of claim 1, wherein the method comprises orally administering iptacopan or a pharmaceutically acceptable salt thereof once daily (q.d.) to the subject.

7. The method of claim 1, wherein the subject has been previously treated, or is currently being treated, with at least one of plasmapheresis, intravenous immunoglobulins (IVIG), rituximab, and bendamustine.

8. The method of claim 1, wherein treating comprises achieving an increase in platelet count by at least 10 k/uL, relative to prior to treatment; or achieving a platelet count of at least 50 k/uL.

9. The method of claim 1, wherein treating comprises achieving a reduction in bleeding.

10. The method of claim 1, wherein treating comprises maintaining an increase in platelet count for at least about 1 week.

11. The method of claim 1, wherein treating comprises achieving an increase in hemoglobin level by at least 1.5 g/dL relative to prior to treatment; or achieving a hemoglobin level of at least 10 g/dL.

12. The method of claim 1, wherein treating comprises achieving a reduction in transfusion requirements relative to prior to treatment.

13. The method of claim 1, wherein treating comprises maintaining hemoglobin level for at least about 1 week.

14. The method of claim 1, wherein treating comprises achieving a reduction in fatigue severity relative to prior to treatment.

15. The method of claim 9, wherein treating comprises achieving an improvement of the modified WHO bleeding score by 1, 2, 3, or 4 relative to prior to treatment.

16. The method of claim 1, wherein the subject has been previously treated, or is currently being treated, with complement inhibitor therapy, immunosuppressive therapy, or other therapy prescribed for the treatment of CAD.

17. The method of claim 1, wherein the therapeutically effective amount of iptacopan or a pharmaceutically acceptable salt thereof comprises a dose of about 200 mg, wherein the dosing amount refers to the anhydrous free base of iptacopan hydrochloride.

18. The method of claim 1, wherein the method comprises administering a therapeutically effective amount of iptacopan hydrochloride.

19. The method of claim 1, wherein the method comprises administering a therapeutically effective amount of iptacopan hydrochloride monohydrate.

20. The method of claim 1, wherein the method comprises administering a therapeutically effective amount of iptacopan hydrochloride monohydrate Form $H_B$.

21. The method of claim 1, wherein the method comprises orally administering iptacopan or a pharmaceutically acceptable salt thereof to the subject.

22. The method of claim 1, wherein the therapeutically effective amount of iptacopan or a pharmaceutically acceptable salt thereof is administered once daily (q.d.) to the subject.

* * * * *